(12) United States Patent
Williams et al.

(10) Patent No.: US 10,577,308 B2
(45) Date of Patent: Mar. 3, 2020

(54) SODIUM CHANNEL MODULATORS

(71) Applicants: The Florey Institute of Neuroscience and Mental Health, Melbourne (AU); The University of Melbourne, Victoria (AU)

(72) Inventors: Spencer John Williams, Coburg (AU); Bevyn Jarrott, Mount Martha (AU)

(73) Assignees: The Florey Institute, Melbourne (AU); The University of Melbourne, Victoria (AU)

( * ) Notice: Subject to any disclaimer, the term of this patent is extended or adjusted under 35 U.S.C. 154(b) by 0 days.

(21) Appl. No.: 15/561,674

(22) PCT Filed: Mar. 24, 2016

(86) PCT No.: PCT/AU2016/050222
§ 371 (c)(1),
(2) Date: Sep. 26, 2017

(87) PCT Pub. No.: WO2016/149765
PCT Pub. Date: Sep. 29, 2016

(65) Prior Publication Data
US 2018/0072656 A1 Mar. 15, 2018

(30) Foreign Application Priority Data
Mar. 26, 2015 (AU) ................................ 2015901096

(51) Int. Cl.
| *C07D 213/36* | (2006.01) |
| *C07C 217/18* | (2006.01) |
| *C07D 231/56* | (2006.01) |
| *C07D 239/26* | (2006.01) |
| *C07D 403/12* | (2006.01) |
| *C07D 401/14* | (2006.01) |
| *C07D 271/06* | (2006.01) |
| *C07C 255/58* | (2006.01) |
| *C07C 217/58* | (2006.01) |
| *C07C 233/43* | (2006.01) |
| *C07C 311/37* | (2006.01) |
| *C07C 311/16* | (2006.01) |

(52) U.S. Cl.
CPC .......... *C07C 217/18* (2013.01); *C07C 217/58* (2013.01); *C07C 233/43* (2013.01); *C07C 255/58* (2013.01); *C07C 311/16* (2013.01); *C07C 311/37* (2013.01); *C07D 213/36* (2013.01); *C07D 231/56* (2013.01); *C07D 239/26* (2013.01); *C07D 271/06* (2013.01); *C07D 401/14* (2013.01); *C07D 403/12* (2013.01)

(58) Field of Classification Search
CPC .................................................. C07D 213/36
See application file for complete search history.

(56) References Cited

U.S. PATENT DOCUMENTS

| 3,960,878 A * | 6/1976 | Petersen | C07D 213/38 |
| | | | 546/300 |
| 4,588,735 A * | 5/1986 | Spatz | A01N 43/40 |
| | | | 514/357 |
| 5,767,132 A * | 6/1998 | Bottcher | C07C 217/16 |
| | | | 514/337 |
| 6,420,354 B1 | 7/2002 | Marquess et al. | |

FOREIGN PATENT DOCUMENTS

| WO | 1995/029152 A1 | 11/1995 | |
| WO | WO-2005014588 A1 * | 2/2005 | ........... C07D 409/04 |
| WO | 2009/055869 A1 | 5/2009 | |
| WO | 2010/006704 A1 | 1/2010 | |
| WO | 2012/085586 A1 | 6/2012 | |
| WO | 2013/185764 A2 | 12/2013 | |
| WO | 2014/099705 A1 | 6/2014 | |

OTHER PUBLICATIONS

Chemical Abstracts Registry No. 2007-71-8, indexed in the Registry file on STN CAS Online on Nov. 16, 1984 (Year: 1984).*
PubChem CID 60684686, National Center for Biotechnology Information. PubChem Compound Database; CID=60684686, https://pubchem.ncbi.nlm.nih.gov/compound/60684686 (accessed Nov. 29, 2018), create date Oct. 18, 2012. (Year: 2012).*
PubChem CID 60633427, National Center for Biotechnology Information. PubChem Compound Database; CID=60633427, https://pubchem.ncbi.nlm.nih.gov/compound/60633427 (accessed Nov. 29, 2018), create date Oct. 18, 2012 (Year: 2012).*
Chemical Abstracts Registry No. 1648417-57-5 {indexed in the Registry file on STN CAS Online Feb. 16, 2015. (Year: 2015).*
Chemical Abstracts Registry No. 1244859-47-9 {indexed in the Registry file on STN CAS Online Oct. 3, 2010. (Year: 2010).*
Chemical Abstracts Registry No. 1175965-25-9 {indexed in the Registry file on STN CAS Online Aug. 26, 2009. (Year: 2009).*
Chemical Abstracts Registry No. 1181973-72-7 {indexed in the Registry file on STN CAS Online Sep. 10, 2010. (Year: 2010).*
Ou, W. et al., "Asymmetric Synthesis of Nonracemic Primary Amines via Spiroborate-Catalyzed Reduction of Pure(E)- and (Z)-O-Benzyloximes: Applications toward the Synthesis of Calcimimetic Agents", Journal of Organic Chemistry (2013), 78(11), pp. 5314-5327.

(Continued)

*Primary Examiner* — Laura L Stockton
(74) *Attorney, Agent, or Firm* — Banner & Witcoff, Ltd.

(57) ABSTRACT

The present disclosure relates generally to compounds having activity as voltage-gated sodium channel blockers and their use in the field of therapeutic treatment, including the therapy or management of conditions associated with excessive, unwanted, inadequate or otherwise undesirable sodium ion passage through cellular membranes via voltage-gated sodium channels. In some embodiments, the disclosure relates to aryloxy-substituted amines for use as sodium channel blockers or modulators. Methods for their manufacture and compositions containing the compounds are also disclosed.

5 Claims, 1 Drawing Sheet

(56) References Cited

OTHER PUBLICATIONS

Namdev, D. et al., "Identification of forced degradation products of tamsulosin using liquid chromatography/electrospray ionization tandem mass spectrometry", Journal of Pharamceutical and Biomedical Analysis, Jan. 25, 2014, vol. 88, pp. 245-255.
Besace, Y., "1-Amino-4-aryloxy-2-butynes", Bulletin de la Societe Chimique de France, 1971, No. 5, pp. 1793-1796.
International Search Report and Wrriten Opinion issued from corresponding PCT/AU2016/050222, dated May 27, 2016.

\* cited by examiner

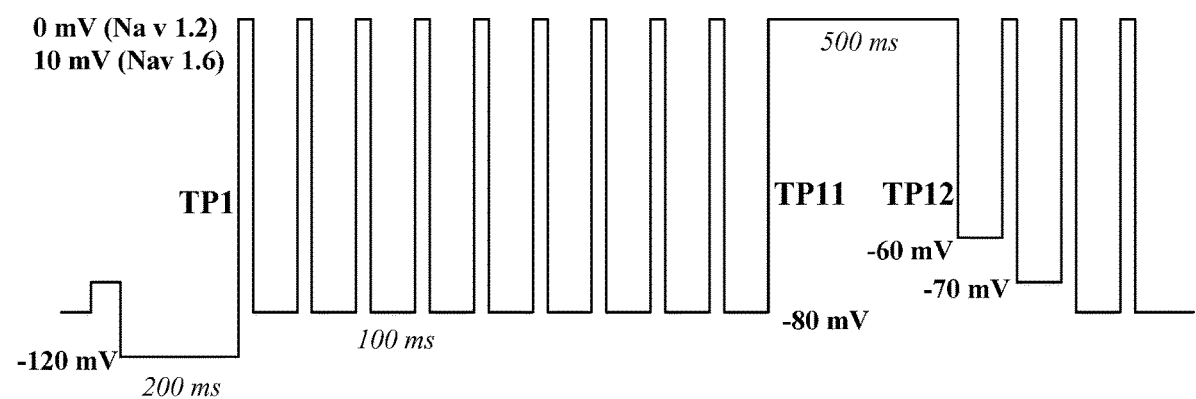

SODIUM CHANNEL MODULATORS

RELATED APPLICATIONS

This application is a National Stage Application under 35 U.S.C. 371 of co-pending PCT application PCT/AU2016/050222 designating the United States and filed Mar. 24, 2016; which claims the benefit of AU application number 2015901096 and filed Mar. 26, 2015.

FIELD

The present disclosure relates generally to compounds having activity as voltage-gated sodium channel blockers and their use in the field of therapeutic treatment, including the therapy or management of conditions associated with excessive, unwanted, inadequate or otherwise undesirable sodium ion passage through cellular membranes via voltage-gated sodium channels. In some embodiments, the disclosure relates to aryloxy-substituted amines for use as sodium channel blockers or modulators. Methods for their manufacture and compositions containing the compounds are also disclosed.

BACKGROUND

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The electrical potential difference across a neuronal cell membrane is the result of an inequitable distribution of ions on either side of the membrane. In its resting state, a neuron has a high internal store of potassium ions ($K^+$) with sodium ions ($Na^+$) accumulated on the outside of the membrane. In such a state, the flow of ions across a membrane through non-gated channels is such that their movement causes no net change in charge. However, a perturbation of this resting flow results in an alteration of the membrane's potential.

Sodium channels are aqueous pores in the cellular membrane that regulate and provide a selective passage for sodium ions between the internal and external environments of a cell. Voltage-gated sodium ($Na_v$) channels, i.e. those opened by changes in membrane potential, are largely responsible for the depolarization of the cell. When closed, they help maintain the neuron's resting potential, and when open, allow sodium ions to flow down the electrochemical gradient and depolarize the cell.

$Na_v$ channels are formed by proteins embedded within the cell's membrane and are typically complexes of a large glycoprotein called the α-subunit, which forms the channel's pore, and auxiliary β-subunits, which regulate the function of the α-subunit. γ- and δ-Subunits may also exist to regulate the α-subunit.

The α-subunit has four repeats, labelled I through IV, of the same 150 amino acid sequence. Each repeat contains six membrane-spanning regions labelled S1 through S6. The highly conserved S4 region, thought to be part of the channel that acts as its voltage sensor, has a positive amino acid at every third position, with hydrophobic residues between these. It is thought that when stimulated by a change in transmembrane voltage, this subunit moves from within the pore toward the extracellular side of the cell, allowing the channel to become permeable to ions that would otherwise have been blocked by the subunit's positive charges. This is sometimes referred to as the "activation gate". Another "plug" located on the internal side of the channel is known as the "inactivation gate".

The inner pore of $Na_v$ channels contains a selectivity filter made of negatively charged amino acid residues (aspartic acid and glutamic acid), which attract the positive $Na^+$ ion and keep out negatively charged ions such as chloride. The mouth of the pore is some 1.2 nm wide, narrowing to about 0.3 by 0.5 nm wide, which is just large enough to allow a single $Na^+$ ion with a water molecule associated to pass through whilst being small enough to exclude larger $K^+$ ions. Different sized ions also cannot interact as well with the negatively charged glutamic acid residues that line the pore.

$Na_v$ channels exist in three conformational states: resting (closed), activated (open), and inactivated (closed).

In their resting state $Na_v$ channels are blocked on their extracellular side by the activation gate, the inactivation gate is open and the inside of the neuron is negatively charged relative to the outside. This difference in membrane potential is referred to as the resting potential (−70 mV).

In the activated state, opening of $Na_v$ channels in response to an electrical stimulus results in a rapid influx of sodium ions, causing more $Na_v$ channels to open and the cell becomes more positively charged (depolarized). In healthy neurons, the activated state is unstable and will rapidly transition to the inactivated state.

The inactivated state is achieved shortly after the sodium channel has been activated, when the internal inactivation gate then blocks the inside of the $Na_v$ channel while an outflow of potassium ions through voltage-gated potassium channels restores the membrane potential to its resting value. Although the external activation gate is open, sodium ions cannot flow through into the cell. Rapid inactivation is crucial for the normal activity of the cell.

Finally, the inactivation gate opens and the activation gate closes bringing the $Na_v$ channel back to its resting state. This places the channels in readiness to be activated again during the next action potential.

This process of transition between the conformational states (referred to as gating) occurs in the space of 2-3 milliseconds and in this manner, changes in membrane potential are propagated along the membrane from the point of stimulation. A self-propagating wave of depolarization down the axon of a neuron is known as an action potential. The more $Na_v$ channels that exist in a neuron's membrane, the faster the action potential will propagate down the axon. When it reaches the end of the axon, the action potential may electrically stimulate the membrane of an adjacent cell or release neurotransmitters into the synaptic cleft, which chemically open gated channels in the adjacent cell membrane. It is the rapid cycling through the resting, activated and inactivated states that allow them to sustain rapid trains of action potential. Thus, $Na_v$ channels are critical for the initiation and propagation of action potentials in neurons and, ultimately, the electrical activity of the central and peripheral nervous systems.

Nine distinct α-subunits of voltage gated sodium channels have been identified and their corresponding channels are known as $Na_v1.1$-$Na_v1.9$. These subtypes share more than 50% amino acid identity within the membrane-spanning domains and extracellular loops, and can be distinguished not only by differences in their sequence but also by their kinetics and expression profiles, as well as tissue localization. The tissue localizations of the nine isoforms vary greatly. $Na_v$ 1.4 is the primary sodium channel of skeletal muscle, and $Na_v$ 1.5 is primary sodium channel of cardiac myocytes. Na$_v$s 1.7, 1.8 and 1.9 are primarily localized to the peripheral nervous system, while Na$_v$s 1.1, 1.2, 1.3, and 1.6 are channels found in the central or central and peripheral nervous systems.

Notwithstanding the essential role of voltage-gated sodium channels in the central and peripheral nervous systems, it is now well established that they are also implicated in the aetiology and/or symptoms of various neuronal diseases and disorders (neuropathies). Perturbations of the normal gating cycle can lead to hyperexcitability (excessive firing of the cell), which is implicated in a number of neuropathies such as migraine, epilepsy, neuropathic pain and neurodegenerative diseases (Eijkelkamp N., et al, *Brain*, 2012, 135, 2585-2512)

Depending on the particular nerves involved, the neuropathy can be classified as a central or peripheral neuropathy. Central neuropathies arise from spinal cord, brainstem, thalamic, and cerebral damage or disease, while peripheral neuropathies arise from damage or disease of peripheral nerves.

The peripheral nervous system transmits information from the brain and spinal cord to every other part of the body. More than 100 types of peripheral neuropathy have been identified, each with its own characteristic set of symptoms, pattern of development, and prognosis. Impaired function and symptoms depend on the type of nerves—motor, sensory, or autonomic—that are damaged. Some people may experience temporary numbness, tingling, and pricking sensations, sensitivity to touch, or muscle weakness. Others may suffer more extreme symptoms, including burning pain (especially at night), muscle wasting, paralysis, or organ or gland dysfunction. Peripheral neuropathy may be either inherited or acquired. Causes of acquired peripheral neuropathy include systemic diseases (e.g. diabetes), physical injury (trauma) to a nerve, tumors, toxins, autoimmune responses, viral and bacterial infections, nutritional deficiencies, alcoholism, and vascular and metabolic disorders. Inherited forms of peripheral neuropathy are caused by genetic mutations.

Central neuropathy, as the name implies, is the result of damage to the central nervous system, i.e. brain and spinal cord. As with peripheral neuropathies, the causes are varied and include physical injury, disease and autoimmune responses.

A particular example of such a neuropathy is multiple sclerosis (MS), which is a chronic, often disabling, disease that randomly attacks the central nervous system. The progress, severity and specific symptoms of the disease cannot be predicted; symptoms may range from tingling and numbness to paralysis and blindness. MS is a devastating disease because people live with its unpredictable physical and emotional effects for the rest of their lives. Symptoms of MS are unpredictable and vary greatly from person to person and from time to time in the same person. They may include: fatigue, impaired vision, loss of balance and muscle coordination, slurred speech, tremors, stiffness, bladder and bowel problems, difficulty walking, short-term memory loss, mood swings and, in severe cases, partial or complete paralysis.

A significant contributor to non-remitting deficits in demyelinating neuroinflammatory diseases such as MS and the related Guillain-Barre's syndrome (GBS), and their respective animal models, experimental allergic encephalomyelitis (EAE) and experimental autoimmune neuritis (EAN), is axonal loss. Recent studies have demonstrated that persistently activated sodium channels can trigger axonal injury by providing a sustained sodium influx that can drive reverse sodium-calcium exchange and sodium channel blockade can prevent axonal degeneration within white matter tracts in a variety of disease models. In addition, it has been demonstrated that the sodium channel blocker phenytoin inhibits immune cells in the neuroinflammatory disorders and that administration of the sodium channel blocker flecainide in the EAN model, significantly increased the number of functional axons and significantly decreased axonal loss.

Physical trauma (car accident, gunshot, falls, etc.) or disease (polio, spina bifida, Friedreich's Ataxia, etc.) can lead to spinal cord injury (SCI)—damage to the spinal cord that results in a loss of function such as mobility or feeling. The spinal cord does not have to be severed in order for a loss of functioning to occur. In fact, in most people with SCI, the spinal cord is intact, but the damage to it results in loss of function. The extent of loss of function will vary depending on the area of injury but can range from quadriplegia, partial loss of function or dexterity in the arms and hands, paraplegia, poor trunk control as the result of lack of abdominal muscle control and reduced control of the hip flexors and legs. Besides a loss of sensation or motor functioning, individuals with SCI also experience other changes. For example, they may experience dysfunction of the bowel and bladder. Very high injuries (C-1, C-2) can result in a loss of many involuntary functions including the ability to breathe, necessitating breathing aids such as mechanical ventilators or diaphragmatic pacemakers. Other effects of SCI may include low blood pressure, inability to regulate blood pressure effectively, reduced control of body temperature, inability to sweat below the level of injury, and chronic pain.

Secondary cell injury due to spinal cord trauma results, in part, from the accumulation of calcium ions within injured neurons and their axons. As noted above, this arises due to reverse operation of the sodium-calcium exchanger, which in turn is triggered by an increase in intracellular sodium concentration via persistently activated voltage-gated sodium channels. Pharmacological blockade of sodium channels has been shown to prevent axonal degeneration and preserve function after injury to central nervous system white matter tracts.

Many peripheral or central neuropathic conditions commonly result in pain. Pain can be classed as acute (or nociceptive) or neuropathic.

Nociceptive pain is mediated by thermal, mechanical, electrical or chemical stimulation of pain receptors, known as nociceptors, which are located in skin, bone, connective tissue, muscle and viscera. Its purpose is to serve as a warning of potential ongoing tissue damage and is experienced in and around the point of injury. It usually responds to opioid and/or NSAID treatment. In the main, as healing progresses, the pain and inflammation associated with an injury abates and resolves.

In contrast, individuals may experience pain in the absence of an obvious tissue injury, or suffer (either continuously or periodically) chronic or protracted pain long after the injured tissue is apparently healed. Such pain serves no protective function and is predominantly neuropathic in nature, thus referred to as neuropathic pain, or chronic (nerve) pain. Neuropathic pain has been variously described as pain that results from a pathologic change in nerves or pain initiated or caused by a primary lesion or dysfunction in the nervous system (Mersky and Bogduk, *Classifications of Chronic Pain*, 2$^{nd}$ Ed., Seattle IASP Press: 1994, 394; De Andres and Garcia-Ribas, *Pain Practice*, 2003, 3:1-7) and can be described as burning, electric, tingling and shooting in nature. Neuropathic pain is associated with a variety of disease states and presents in the clinic with a wide range of symptoms (Woolf and Mannion, *Lancet,* 1999, 353:1959-64). The damage to the nerves may be caused by accidental or surgical injury, by metabolic disturbances such as diabetes or vitamin B12 or other nutrient deficiency, by ischaemia, by radiation, by autoimmune attack, by cytotoxic drugs used in cancer chemotherapy by alcohol, by infections, especially viral infections, particularly with the herpes virus, by tumours, by degenerative diseases, or by unknown factors such as may be operative in trigeminal and other neuralgias. Neuropathic pain does not require specific pain receptor stimulation although such stimulation can add to the intensity of the pain sensation.

Neuropathic pain is often characterised by chronic allodynia and/or hyperalgesia. Allodynia is pain resulting from a non-noxious stimulus, i.e. a stimulus that does not ordinarily cause a painful response, e.g. a light touch. Hyperalgesia, on the other hand, is an increased sensitivity to noxious stimuli (injury), i.e. a greater than normal pain response, and can be further defined as primary, occurring immediately in the vicinity of an injury, or secondary, occurring in undamaged area remote from an injury. Neuropathic pain is usually unresponsive to treatments used for nociceptive pain.

It is estimated that neuropathic pain affects over 26 million people worldwide and despite its common occurrence, remains one of the most poorly understood and untreated conditions in primary care, and can have a debilitating effect on almost all aspects of a sufferer's life. It has been associated with depression, anxiety, loss of independence and can impact on an individual's relationships and ability to work. The annual cost of neuropathic pain in the United States alone, including medical expenses, lost income and lost productivity is estimated to be $100 billion. The condition is particularly prevalent amongst the elderly and is experienced by a significant proportion of patients suffering from other disease states such as diabetes and advanced cancer.

Sodium channel blockers have been reported as potentially useful agents in the treatment of neuropathic pain (Tanelian et al, *Pain Forum,* 1995, 4(22):75-80; Kyle and Ilyin, *J. Med. Chem.,* 50: 2583-8, 2007; Ilyin, et al, *J. Pharmacol. Exper. Ther.,* 2006, 318:1083-93). There is evidence that sodium channel blockers selectively suppress etopic neural firing in injured (unmyelinated) nerves, which have an accumulation of sodium channels, and studies carried out on known blockers, such as carbamazepine, phenytoin, lidocaine and mexiletine, have demonstrated utility in the treatment of various types of neuropathic pain. Consistent with this, is the demonstration that sodium channels accumulate in the peripheral nerve sites of axonal injury and also in second order sensory neurons in pain pathways in the spinal cord. Alterations in the either the level of expression or distribution of sodium channels within an injured nerve, therefore, have a major influence on the pathophysiology of pain associated with this type of trauma.

Epilepsy is a disorder arising from abnormal or excessive bursts of electrical activity (firing) in the brain, which manifests as recurring seizures over a period of time. A person can develop epilepsy at any age. While many sufferers will experience at least one seizure before adulthood, a rapidly growing demographic is the over 55 years population, prone to cerebrovascular, respiratory and cardiac events that can lead to seizures. While the recurrence of seizures is conveniently described by a single term, the disorder can be further categorised by the seizure types of varying aetiologies, such as infections (e.g. meningitis and encephalitis), lack of oxygen, brain injury, brain tumours and neurodegenerative diseases. Susceptibility to or development of epilepsy may also be due to genetic factors, particularly in children. Mutations in genes encoding neuronal voltage-gated sodium channels are the most common known genetic cause of epilepsy, and are implicated in severe myoclonic epilepsy of infancy (SMEI), generalized epilepsy with febrile seizures plus (GEFS+), simple febrile seizures, benign familial infantile seizures (BFIS), and benign familial neonatal-infantile seizures (BFNIS).

Seizures typically fall into two categories: partial or focal seizures, and generalised seizures.

Partial or focal seizures commence in a focal point of the brain and therefore affect the part of the body that is controlled by that part of the brain. These types of seizures can be the result of tumours, stroke or head injury.

Partial or focal seizures may then be further categorised. Simple partial seizures affect only one part of the brain and the symptoms are dependent upon the corresponding brain function. The sufferer usually remains alert during the seizure, which is of relatively short duration, and may involve involuntary movement or spasm of limbs, sensory disturbances, feelings of déjà vu or feelings of nausea. Complex partial seizures start in a small area of the temporal or frontal lobes and cause an impairment of awareness or responsiveness, in which the conscious state is altered, rather than lost. Memory loss is sometimes associated with complex partial seizures.

Primary generalised seizures involve the whole brain and thus affect the whole body. Genetic factors typically govern these types of seizures. Primary generalised seizures produce loss of consciousness either briefly or for a longer period of time, and are further sub-categorized into several major types, some convulsive and some non-convulsive.

Absence seizures (petit mal seizures) are non-convulsive. The seizure manifests as starring or fluttering of eyelids and usually lasts only several seconds. Atonic seizures affect muscle tone causing the person to collapse. Myoclonic seizures are brief shock-like jerks of muscles. Tonic seizures result in sudden stiffening movements. Tonic-clonic seizures (grand mal seizures) may last several minutes. The subject's body stiffens and falls, and their limbs jerk in rhythmic movements.

Secondary generalised seizures occur when a disturbance occurs in a focal part of the brain (partial seizure) but then spreads throughout the brain.

In humans, $Na_v1.2$ mutations are associated with inherited epilepsy (Heron, et al, *Lancet,* 2002, 360:851-2) and other forms of epilepsy, such as generalised epilepsy with febrile seizures (Sugawara, et al, *Proc Natl Acad Sci USA,* 2001, 98:6384-9)

Studies have shown that protection from seizures can be achieved by inhibition of sodium channels, in particular $Na_v1.1$ and $Na_v1.2$ channels. For example, blocking high-frequency repetitive spike firing, believed to occur during the spread of seizure activity helps protect against generalized tonic clonic and partial seizures. (Rogawski and Loscher, *Nature Reviews,* 2004, 5:553-64, and references therein).

Current therapies involve anticonvulsant drugs, also known as anti-epileptic drugs (AEDs), which modify the bursting properties of neurons and reduce synchronization in localized neuronal ensembles, as well as inhibiting the spread of abnormal firing to distant sites. Nevertheless, a proportion of patients continue to experience seizures, and/or suffer from unwanted side effects.

Abnormalities of neuronal excitability are also implicated in migraine, and sodium channel blockers have been postulated as having potential use in its treatment and/or prevention, with controlled clinical trials suggesting that certain $Na_v$ blocker anti-eplilepic drugs prevent migraine (Mantegazza, M., et al, *Lancet Neurol* 2010, 9:413-424, and references cited therein).

Sodium channels, particularly $Na_v1.1$, $Na_v1.5$ and $Na_v1.6$ are also up-regulated in models of autoimmune and inflammatory disorders and thus may be implicated in such disorders.

In recent years there has been increasing evidence correlating the function of ion channels with cancer progression, and sodium channel activity has been clearly associated with invasion and metastasis behaviours of several types of cancer, including breast, colon, lung, ovary and prostate. Prostate cancer cells have been reported to overexpress $Na_v1.7$ subunits, whereas $Na_v1.5$ is overexpressed in breast, colon and ovary cancer cells. (Hermandez-Plata, E., et al, *International J Cancer*, 2012, 130: 2013-2023, and the references therein). It has also been observed that voltage-gated sodium channels are up-regulated in strongly metastatic cancers and that inhibiting these channels suppresses tumour cell motility and invasiveness in breast, prostate, lung and cervical cancers (Onkal, R., et al, *European J Pharm*, 2009, 625: 206-219. Hermandez-Plata, E., et al (*International J Cancer*, 2012, 130: 2013-2023) also demonstrated that a selective $Na_v1.6$ inhibitor reduced in vitro invasiveness of primary cultures from human cervical cancers.

An increasing body of evidence correlates abnormal expression and function of sodium channels with disorders such as neuropathic pain, multiple sclerosis, epilepsy, migraine and cancer, and data already indicates that sodium channel blockers are efficacious for a range of diseases and disorders (Mantegazza, M., et al, supra). Given the individual and social impact of these diseases and disorders and other conditions in which excessive, undesirable or otherwise unwanted sodium channel activity is involved or implicated, there remains the need for new therapies that may ameliorate, relieve, prevent or otherwise improve one or more of their symptoms, or the conditions themselves.

Thus, compounds that can inhibit or otherwise modulate undesirable activity, such as excessive firing, of one or more voltage-gated sodium channel sub-types may be useful in the treatment and/or prevention of neuropathies or diseases associated with such activity.

SUMMARY

It has now been found that certain aryloxyamine compounds may possess inhibitory or blocking activity against one or more sodium channel sub-types. Accordingly, the aryloxyamine compounds of the disclosure may have utility in the prevention, therapy or management of diseases or disorders, and/or one or more of their symptoms, mediated by sodium channel activity, that is, with which undesirable, excessive or unwanted sodium channel activity is associated, and which are responsive to sodium channel inhibition.

Accordingly, in a first aspect, the present disclosure provides a compound of Formula (I):

wherein

A is an optionally substituted cyclopentadi-2,4-en-1-yl or phenyl group, an optionally substituted 5-6-membered monocyclic heteroaryl group, an optionally substituted naphthyl group or an optionally substituted 9-10-membered bicyclic heteroaryl group;

$L_1$ is an optionally substituted $C_{1-4}$ alkylene group, an optionally substituted $C_{2-4}$ alkenylene group or an optionally substituted $C_2$-$C_4$ alkynylene group;

$L_2$ is an optionally substituted $C_{1-4}$ alkylene group, an optionally substituted $C_{2-4}$ alkenylene group or an optionally substituted $C_2$-$C_4$ alkynylene group or a —$CO_2$— group;

R is hydrogen or a $C_{1-6}$alkyl group; and

B is an optionally substituted cyclopentadi-2,4-en-1-yl or phenyl group, an optionally substituted 5-6-membered monocyclic heteroaryl group, an optionally substituted naphthyl group; or an optionally substituted 9-10-membered fused bicyclic heteroaryl group;

provided that when $L_2$ is $CH_2$, then B is not a group of the formula:

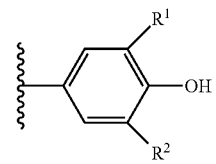

(a)

wherein $R^1$ and $R^2$ are independently selected from hydrogen, $C_{1-6}$ alkyl and $C_{3-6}$ cycloalkyl;

or a pharmaceutically acceptable salt or solvate thereof.

In another aspect, the disclosure provides a compound of Formula (I) wherein A, $L_1$, $L_2$, R, and B are as defined above, provided that B is not a group of formula (a) wherein $R^1$ and $R^2$ are independently selected from hydrogen, $C_{1-6}$ alkyl and $C_{3-6}$ cycloalkyl.

In another aspect, the disclosure provides a compound of Formula (I) wherein A, $L_1$, $L_2$, R, and B are as defined above, provided that when $L_2$ is $CH_2$, B is not a group of formula (a) wherein $R^1$ and $R^2$ are independently selected from hydrogen, $C_{1-6}$ alkyl and $C_{3-6}$ cycloalkyl, but are not both hydrogen.

In another aspect, the disclosure provides a compound of Formula (I) wherein A, $L_1$, $L_2$, R, and B are as defined above, provided that B is not a group of formula (a) wherein $R^1$ and $R^2$ are independently selected from hydrogen, $C_{1-6}$ alkyl and $C_{3-6}$ cycloalkyl, but are not both hydrogen.

In another aspect, the disclosure provides a composition comprising a compound of Formula (I) or a pharmaceutically acceptable salt or solvate thereof together with a pharmaceutically acceptable additive. The composition may be for use in the treatment of a disease or disorder that is mediated by sodium channel activity.

Yet another aspect of the disclosure relates to a method for preventing sodium ion influx into a cell by blocking or modulating the activity of one or more sodium channel sub-types, said method comprising contacting said cell with a compound of Formula (I) or a pharmaceutically acceptable salt or solvate thereof.

Another aspect of the disclosure relates to a method for treating a disease or disorder which is mediated by sodium channel activity, in a subject in need thereof, comprising administering to said subject a compound of Formula (I) or a pharmaceutically acceptable salt or solvate thereof.

A further aspect relates to use of a compound of Formula (I) or a pharmaceutically acceptable salt or solvate thereof in the manufacture of a medicament for treating a disease or disorder that is mediated by sodium channel activity.

Another aspect provides a compound of Formula (I) or a pharmaceutically acceptable salt or solvate thereof for use in treating a disease or disorder that is mediated by sodium channel activity.

Another aspect provides use of a compound of Formula (I) or a pharmaceutically acceptable salt or solvate thereof in the treatment of a disease or disorder that is mediated by sodium channel activity.

In some embodiments of the disclosure, some of these compounds may inhibit the activity of the $Na_v1.2$ sodium channel. In further embodiments, such compounds may selectively inhibit the activity of the $Na_v1.2$ sodium channel relative to one or more other subtypes, such as $Na_v1.6$. In other embodiments of the disclosure some of these compounds may inhibit the activity of the $Na_v1.6$ sodium channel. In further embodiments thereof, some of these compounds may selectively inhibit the activity of the $Na_v1.6$ sodium channel relative to one or more other subtypes, such as $Na_v1.2$.

In some embodiments, the disease or disorder is an epileptic disorder, multiple sclerosis, migraine or neuropathic pain.

BRIEF DESCRIPTION OF THE FIGURES

FIG. 1 depicts the voltage sequence used to measure inhibitory activity of compounds as described in Example 3. An automated patch clamp screening assay was used to measure the inhibitory effect (potency) of compounds in three conformational states of the sodium channel: (1) the tonic state (TP1); (2) the frequency-dependent (10 Hz) state (TP11) and (3) the inactivated state (TP12).

DETAILED DESCRIPTION

Throughout this specification and the claims that follow, unless the context requires otherwise, the word "comprise" and variations such as "comprises" and "comprising" will be understood to imply the inclusion of a stated integer or step or group of integers but not the exclusion of any other integer or step or group of integers.

Throughout this specification and the claims that follow, unless the context requires otherwise, the phrase "consisting essentially of", and variations such as "consists essentially of" will be understood to indicate that the recited element(s) is/are essential i.e. necessary elements of the invention. The phrase allows for the presence of other non-recited elements that do not materially affect the characteristics of the invention but excludes additional unspecified elements that would affect the basic and novel characteristics of the method defined.

The singular forms "a", "an" and "the" include plural aspects unless the context clearly dictates otherwise.

The term "invention" includes all aspects, embodiments and examples as described herein.

As used herein, the term "alkyl" or "alk", used either alone or in compound words denotes straight chain, or branched alkyl, preferably $C_{1-20}$ alkyl, e.g. $C_{1-10}$ or $C_{1-6}$. Examples of straight chain and branched alkyl include methyl, ethyl, n-propyl, isopropyl, n-butyl, sec-butyl, t-butyl, n-pentyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propylocytl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Where an alkyl group is referred to generally as "propyl", butyl" etc, it will be understood that this can refer to any of straight or branched isomers where appropriate. An alkyl group may be optionally substituted by one or more optional substituents as herein defined, e.g. hydroxy or halo.

The term "alkenyl" as used herein denotes groups formed from straight chain or branched hydrocarbon residues containing at least one carbon to carbon double bond including ethylenically mono-, di- or poly-unsaturated alkyl groups as previously defined, preferably $C_{2-20}$ alkenyl (e.g. $C_{2-10}$ or $C_{2-6}$). Examples of alkenyl include vinyl, allyl, 1-methylvinyl, butenyl, iso-butenyl, 3-methyl-2-butenyl, 1-pentenyl, 1-hexenyl, 3-hexenyl, 1-heptenyl, 3-heptenyl, 1-octenyl, 1-nonenyl, 2-nonenyl, 3-nonenyl, 1-decenyl, 3-decenyl, 1,3-butadienyl, 1-4,pentadienyl, 1,3-hexadienyl and 1,4-hexadienyl. An alkenyl group may be optionally substituted by one or more optional substituents as herein defined, e.g. hydroxy or halo.

As used herein the term "alkynyl" denotes groups formed from straight chain or branched hydrocarbon residues containing at least one carbon-carbon triple bond including ethynically mono-, di- or poly-unsaturated alkyl groups as previously defined. Unless the number of carbon atoms is specified the term preferably refers to $C_{2-20}$ alkynyl (e.g. $C_{2-10}$ or $C_{2-6}$). Examples include ethynyl, 1-propynyl, 2-propynyl, and butynyl isomers, and pentynyl isomers. An alkynyl group may be optionally substituted by one or more optional substituents as herein defined, e.g. hydroxy or halo.

An "alkylene", "alkenylene" or "alkynylene" group denotes a divalent form of an alkyl, alkenyl or alkynyl group and may be substituted or unsubstituted. Thus, "$C_{1-4}$ alkylene" refers to straight or, where appropriate, branched, methylene, ethylene, propylene and butylene. "$C_{1-4}$ alkylene" refers to ethenylene, propenylene and butenylene, which may be straight, or as appropriate, branched. "$C_{1-4}$ alkynylene" refers to ethynylene, propynylene and butynylene, which may be straight, or as appropriate, branched.

The term "halogen" ("halo") denotes fluorine, chlorine, bromine or iodine (fluoro, chloro, bromo or iodo).

The term "heteroaryl" includes any of monocyclic or bicyclic, hydrocarbon residues, wherein one or more carbon atoms are replaced by a heteroatom so as to provide an aromatic residue. Monocyclic 5-6-membered heteroaryl refers to a single heteroaryl ring having 5 or 6 ring atoms. Bicyclic 9-10-membered heteroaryl refers to bicyclic heteroaryl ring systems, which may be fused, having a total of 9 or 10 ring atoms. Suitable heteroatoms include, O, N, S, P and Se, particularly O, N and S. Where two or more carbon atoms are replaced, this may be by two or more of the same heteroatom or by different heteroatoms. In particular embodiments of the disclosure, when A is a heteroaryl group, it is attached to the adjacent oxygen atom via a carbon atom. A heteroaryl group may be optionally substituted by one or more optional substituents as defined herein. Optional substituents may reside on a carbon ring atom and/or a nitrogen ring atom.

Suitable examples of monocyclic 5-6-membered heteroaryl groups may include pyrrolyl (2- or 3-), furanyl (2- or 3-), thienyl (2- or 3-), pyrazolyl (3-, 4-, or 5-), imidazolyl (4-, or 5-), oxazolyl (2-, 4-, or 5-), isoxazolyl (3-, 4- or 5-), thiazolyl (4-), isothiazolyl, 1,2,3-triazolyl, 1,2,4-triazolyl, 1,2,3-oxadiazolyl, oxatriazolyl, furazanyl, 1,3,4-thiadiazolyl, tetrazolyl, pyridinyl (2-, 3- or 4-), pyridizinyl (3- or 4-), pyrimidinyl (2-, 4- or 5-) and pyrazinyl (2- or 3-), and triazinyl, (1,2,3-, 1,3,5- or 1,2,4-). A 5-6-membered heteroaryl group may be attached via any ring carbon atom thereof, i.e. at positions 1-, 2-, 3-, 4-, 5- or 6- as appropriate. Some non-limiting exemplary positions are indicated in parentheses above.

Suitable examples of bicyclic 9-10 membered heteroaryl groups may include indolyl, isoindolyl, benzothienyl, isobenzothienyl, benzofuranyl, isobenzofuranyl, quinazolinyl, cinnolinyl, quinolyl, isoquinolyl, quinolinyl, isoquinolinyl, indazolyl, benzimidazolyl, benzthiazolyl, purinyl, quinoxalinyl, 1,8-naphthpyridinyl, phthalazinyl, pteridinyl. Bicyclic groups, including naphthyl, are, in certain embodiments, attached such that the molecule is essentially linear, at a 2- or 3- (or corresponding) position.

Certain groups as described herein, for example the groups A, B, $L_1$ and $L_2$, may each be independently optionally substituted, i.e., they may be unsubstituted or substituted with one or more (e.g. 2, 3, 4 or 5 as permitted), same or different substituents, independently selected from:

alkyl, (e.g. $C_{1-6}$alkyl such as methyl, ethyl, propyl, butyl),
cycloalkyl (e.g. $C_{3-6}$cycloalkyl, such as cyclopropyl, cyclobutyl, cyclopentyl or cyclohexyl),
hydroxyalkyl (e.g. hydroxy$C_{1-6}$alkyl, such as hydroxymethyl, hydroxyethyl, hydroxypropyl),
alkoxyalkyl (e.g. $C_{1-6}$alkoxy$C_{1-6}$alkyl, such as methoxymethyl, methoxyethyl, methoxypropyl, ethoxymethyl, ethoxyethyl, ethoxypropyl),
alkoxy (e.g. $C_{1-6}$alkoxy, such as methoxy, ethoxy, propoxy, butoxy),
alkoxyalkoxy (e.g. $C_{1-6}$alkoxy$C_{1-6}$alkoxy, such as methoxymethoxy, methoxyethoxy, methoxypropoxy, ethoxymethoxy, ethoxyethoxy, ethoxypropoxy, propoxymethoxy, propoxyethoxy, propoxypropoxy),
cycloalkoxy (e.g. cyclopropoxy, cyclobutoxy, cyclopentoxyl, cyclohexyloxy), halo,
haloalkyl (e.g. halo$C_{1-6}$alkyl, such as trifluoromethyl, trichloromethyl, tribromomethyl),
haloalkoxy (e.g. halo$C_{1-6}$alkoxy),
hydroxy,
thiol (—SH),
alkylthio (e.g. —S$C_{1-6}$alkyl),
phenyl (which itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkoxy, $C_{1-6}$alkoxy$C_{1-6}$alkoxy, halo$C_{1-6}$alkyl, halo$C_{1-6}$alkoxy, cyano, nitro, —OC(O)$C_{1-6}$ alkyl, —NH$_2$, —NH$C_{1-6}$alkyl, —NHC(O)$C_{1-6}$alkyl and —N($C_{1-6}$alkyl)($C_{1-6}$alkyl)),
benzyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)($C_{1-6}$alkyl)),
phenoxy (wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)($C_{1-6}$alkyl)),
benzyloxy (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)($C_{1-6}$alkyl)),
5-6-membered heteroaryl, e.g pyridinyl, pyridazinyl, pyrimidinyl or pyrazinyl (wherein 5-6-membered heteroaryl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$ alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)($C_{1-6}$alkyl)),
—NH$_2$,
alkylamino (e.g. —NH$C_{1-6}$alkyl, such as methylamino, ethylamino, propylamino etc),
dialkylamino (e.g. —N($C_{1-6}$alkyl)$_2$, such as dimethylamino, diethylamino, dipropylamino),
acylamino (e.g. —NHC(O)$C_{1-6}$alkyl, such as —NHC(O)CH$_3$),
phenylamino (i.e. —NHphenyl, wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$ alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)$C_{1-6}$alkyl),
nitro,
cyano,
formyl,
acyl, including —C(O)-alkyl (e.g. —C(O)$C_{1-6}$alkyl, such as acetyl),
—O—C(O)-alkyl (e.g. —OC(O)$C_{1-6}$alkyl, such as acetyloxy),
benzoyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)($C_{1-6}$alkyl)),
benzoyloxy (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)($C_{1-6}$alkyl)),
CO$_2$H,
CO$_2$alkyl (e.g. CO$_2$$C_{1-6}$alkyl such as methyl ester, ethyl ester, propyl ester, butyl ester),
CO$_2$phenyl (wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)($C_{1-6}$alkyl)),
CO$_2$benzyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)C$_{1-6}$alkyl, —NH$_2$, —NHC$_{1-6}$alkyl, —NHC(O)C$_{1-6}$alkyl and —N(C$_{1-6}$alkyl)(C$_{1-6}$alkyl)), —CONH$_2$, —C(O)NHphenyl (wherein phenyl itself may be further substituted e.g., by one or more of C$_{1-6}$alkyl, halo, hydroxy, hydroxyC$_{1-6}$alkyl, C$_{1-6}$alkoxy, C$_{1-6}$alkoxyC$_{1-6}$alkyl, C$_{1-6}$alkoxyC$_{1-6}$alkoxy, haloC$_{1-6}$alkyl, haloC$_{1-6}$alkoxy, cyano, nitro, —OC(O)C$_{1-6}$alkyl, —NH$_2$, —NHC$_{1-6}$alkyl, —NHC(O)C$_{1-6}$alkyl and —N(C$_{1-6}$alkyl)(C$_{1-6}$alkyl)), —C(O)NHbenzyl (wherein benzyl itself may be further substituted e.g., by one or more of C$_{1-6}$alkyl, halo, hydroxy, hydroxyC$_{1-6}$alkyl, C$_{1-6}$alkoxy, C$_{1-6}$alkoxyC$_{1-6}$alkyl, C$_{1-6}$alkoxyC$_{1-6}$alkoxy, haloC$_{1-6}$alkyl, haloC$_{1-6}$alkoxy, cyano, nitro, —OC(O)C$_{1-6}$alkyl, —NH$_2$, —NHC$_{1-6}$alkyl, —NHC(O)C$_{1-6}$alkyl and —N(C$_{1-6}$alkyl)(C$_{1-6}$alkyl));

—C(O)NHalkyl (e.g. C(O)NHC$_{1-6}$ alkyl such as methyl ester, ethyl ester, propyl ester, butyl amide);

—C(O)NHdialkyl (e.g. C(O)NH(C$_{1-6}$alkyl)$_2$),

—S(O)NH$_2$;

—S(O)NHalkyl (e.g. S(O)NHC$_{1-6}$ alkyl such as methyl ester, ethyl ester, propyl ester, butyl sulfonamide);

amino alkyl (e.g., HNC$_{1-6}$alkyl-, C$_{1-6}$alkylHN—C$_{1-6}$alkyl- and (C$_{1-6}$alkyl)$_2$N—C$_{1-6}$alkyl-), thio alkyl (e.g., HSC$_{1-6}$alkyl-), carboxyalkyl (e.g., HO$_2$CC$_{1-6}$alkyl-), carboxyesteralkyl (e.g., C$_{1-6}$alkylO$_2$CC$_{1-6}$alkyl-), amidoalkyl (e.g., H$_2$N(O)CC$_{1-6}$alkyl-, H(C$_{1-6}$alkyl)N(O)CC$_{1-6}$alkyl-), formylalkyl (e.g., H(O)CC$_{1-6}$alkyl-), acylalkyl (e.g., C$_{1-6}$alkyl(O)CC$_{1-6}$alkyl-), nitroalkyl (e.g., O$_2$NC$_{1-6}$alkyl-), replacement of CH$_2$ with C=O, and where 2 carbon atoms (1,2 or 1,3) are substituted by one end each of a —O—(CH$_2$)$_n$—O— or —NH—(CH$_2$)$_n$—NH— group, wherein n is 1 or 2.

Some non-limiting examples of optional substituents for a nitrogen ring atom include C$_{1-6}$alkyl, (e.g., Me, Et, n-Pr, i-Pr, n-Bu, sec-Bu, t-Bu), NHC(O)C$_{1-6}$alkyl, (e.g., Me, Et, n-Pr, i-Pr, n-Bu, sec-Bu, t-Bu) and benzyl.

Some further examples of substituents for A and/or B independently include C$_{1-6}$alkyl, (e.g., Me, Et, n-Pr, i-Pr, n-Bu, sec-Bu, t-Bu), cyclopropyl, OH, C$_{1-6}$alkoxy (e.g., OMe, OEt, On-Pr, Oi-Pr, On-Bu, Osec-Bu, Ot-Bu), halo (Cl, F, Br, I), CN, CF$_3$, NH$_2$, NHC$_{1-6}$alkyl, (e.g. Me, Et, n-Pr, i-Pr, n-Bu, sec-Bu, t-Bu), NHC(O)C$_{1-6}$alkyl (e.g., Me, Et, n-Pr, i-Pr, n-Bu, sec-Bu, t-Bu), SONH$_2$, phenyl optionally substituted by C$_{1-6}$alkyl, (e.g., Me, Et, n-Pr, i-Pr, n-Bu, sec-Bu, t-Bu), cyclopropyl, OH, C$_{1-6}$alkoxy (e.g., OMe, OEt, On-Pr, Oi-Pr, On-Bu, Osec-Bu, Ot-Bu), halo (Cl, F, Br, I), CN, CF$_3$, NH$_2$, NHC$_{1-6}$alkyl (e.g., Me, Et, n-Pr, i-Pr, n-Bu, sec-Bu, t-Bu), NHC(O)C$_{1-6}$alkyl (e.g., Me, Et, n-Pr, i-Pr, n-Bu, sec-Bu, t-Bu), benzyl optionally substituted by C$_{1-6}$alkyl (e.g., Me, Et, n-Pr, i-Pr, n-Bu, sec-Bu, t-Bu), cyclopropyl, OH, C$_{1-6}$alkoxy (e.g., OMe, OEt, On-Pr, Oi-Pr, On-Bu, Osec-Bu, Ot-Bu), halo (Cl, F, Br, I), CN, CF$_3$, NH$_2$, NHC$_{1-6}$alkyl (e.g., Me, Et, n-Pr, i-Pr, n-Bu, sec-Bu, t-Bu), NHC(O)C$_{1-6}$alkyl (e.g., Me, Et, n-Pr, i-Pr, n-Bu, sec-Bu, t-Bu), and pyridinyl, pyridazinyl, pyrimidinyl or pyrazinyl, each optionally substituted by C$_{1-6}$alkyl (e.g., Me, Et, n-Pr, i-Pr, n-Bu, sec-Bu, t-Bu), cyclopropyl, OH, C$_{1-6}$alkoxy (e.g., OMe, OEt, On-Pr, Oi-Pr, On-Bu, Osec-Bu, Ot-Bu), halo (Cl, F, Br, I), CN, CF$_3$, NH$_2$, NHC$_{1-6}$alkyl (e.g., Me, Et, n-Pr, i-Pr, n-Bu, sec-Bu, t-Bu), NHC(O)C$_{1-6}$alkyl (e.g., Me, Et, n-Pr, i-Pr, n-Bu, sec-Bu, t-Bu).

Some examples of substituents for L$_1$ and/or L$_2$ include C$_{1-6}$alkyl, (e.g., Me, Et, n-Pr, i-Pr, n-Bu, sec-Bu, t-Bu), cyclopropyl, OH, C$_{1-6}$alkoxy (e.g., OMe, OEt, On-Pr, Oi-Pr, On-Bu, Osec-Bu, Ot-Bu), halo (Cl, F, Br, I), CN, CF$_3$, NH$_2$, NHC$_{1-6}$alkyl (e.g., Me, Et, n-Pr, i-Pr, n-Bu, sec-Bu, t-Bu), NHC(O)C$_{1-6}$alkyl (e.g., Me, Et, n-Pr, i-Pr, n-Bu, sec-Bu, t-Bu), phenyl optionally substituted by C$_{1-6}$alkyl (e.g., Me, Et, n-Pr, i-Pr, n-Bu, sec-Bu, t-Bu), cyclopropyl, OH, C$_{1-6}$alkoxy (e.g., OMe, OEt, On-Pr, Oi-Pr, On-Bu, Osec-Bu, Ot-Bu), halo (Cl, F, Br, I), CN, CF$_3$, NH$_2$, NHC$_{1-6}$alkyl (e.g., Me, Et, n-Pr, i-Pr, n-Bu, sec-Bu, t-Bu), NHC(O)C$_{1-6}$alkyl, (e.g., Me, Et, n-Pr, i-Pr, n-Bu, sec-Bu, t-Bu), benzyl optionally substituted by C$_{1-6}$alkyl, (e.g., Me, Et, n-Pr, i-Pr, n-Bu, sec-Bu, t-Bu), cyclopropyl, OH, C$_{1-6}$alkoxy (e.g., OMe, OEt, On-Pr, Oi-Pr, On-Bu, Osec-Bu, Ot-Bu), halo (Cl, F, Br, I), CN, CF$_3$, NH$_2$, NHC$_{1-6}$alkyl (e.g., Me, Et, n-Pr, i-Pr, n-Bu, sec-Bu, t-Bu), NHC(O)C$_{1-6}$alkyl (e.g., Me, Et, n-Pr, i-Pr, n-Bu, sec-Bu, t-Bu), and pyridinyl, pyridazinyl, pyrimidinyl or pyrazinyl, each optionally substituted by C$_{1-6}$alkyl, (e.g., Me, Et, n-Pr, i-Pr, n-Bu, sec-Bu, t-Bu), cyclopropyl, OH, C$_{1-6}$alkoxy (e.g., OMe, OEt, On-Pr, Oi-Pr, On-Bu, Osec-Bu, Ot-Bu), halo (Cl, F, Br, I), CN, CF$_3$, NH$_2$, NHC$_{1-6}$alkyl (e.g., Me, Et, n-Pr, i-Pr, n-Bu, sec-Bu, t-Bu), NHC(O)C$_{1-6}$alkyl (e.g., Me, Et, n-Pr, i-Pr, n-Bu, sec-Bu, t-Bu).

In some examples, A and/or B is further substituted by a phenyl group or 5-6-membered heteroaryl, each of which may be further optionally substituted, to form a 10-12-membered bi-aryl group comprising two covalently linked aryl groups independently selected from optionally substituted phenyl and optionally substituted 5-6-membered heteroaryl. In some embodiments, 10-12-membered bi-aryl is a bi-phenyl group, wherein each phenyl group may be independently optionally substituted as described herein. Thus, in further examples, both phenyl groups are unsubstituted. In other examples, one phenyl group is substituted and the other is unsubstituted. In still other examples, both phenyl groups are substituted, by the same or diffrent substituents. In other embodiments, 10-12-membered bi-aryl is an optionally substituted phenyl group directly covalently linked to an optionally substituted 5-6-membered heteroaryl group, such as an optionally substituted pyridinyl, pyridazinyl, pyrimidinyl or pyrazinyl group. In these embodiments, the phenyl group may be directly attached to L$_2$ or the 5-6-membered heteroaryl group may be directly bonded to L$_2$. In still other embodiments, the 10-12-membered bi-aryl is an optionally substituted 5-6-membered heteroaryl group directly covalently linked to an optionally substituted 5-6-membered heteroaryl group, wherein the 5-6-membered heteroaryl groups may be the same or different. In further examples thereof, the 5-6-membered heteroaryl group is selected from pyridinyl (e.g. optionally substituted 2-, 3- or 4-pyridinyl), pyridazinyl (e.g. optionally substituted 3- or 4-pyridizinyl), pyrimidinyl (e.g. optionally substituted 2-, 4- or 5-pyrimidyl) and pyrazinyl (e.g. optionally substituted 2- or 3-pyrazinyl). In some further examples of embodiments described above, where the first aryl group attached to L$_2$ is a phenyl or 6-membered-heteroaryl group, it is further substituted by the second aryl group at a position ortho or meta to the point of attachment to L$_2$. In some embodiments B is substituted in this manner.

In certain embodiments of the disclosure, A is optionally substituted phenyl or an optionally substituted 6-membered heteroaryl group, such as optionally substituted pyridinyl (e.g. optionally substituted 2-, 3- or 4-pyridinyl) or optionally substituted 2-, 4- or 5-pyrimidyl, or optionally substituted 2- or 3-pyrazinyl, or optionally substituted 3- or 4-pyridizinyl. In some further examples, where valencies allow, A may bear one substituent ortho-, or meta- or para- to the carbon attached to the —O— atom. In further embodiments, where valencies allow, A may bear two substituents, for example, ortho-, ortho; ortho-, meta-; ortho-, para-; meta-, meta- or meta-, para-. In some embodiments, where valencies allow, A may bear 3 substituents.

In further examples, A is substituted at one or both of the positions ortho- to the atom attached to the —O— atom.

In some embodiments, A is a 2,6-disubstituted phenyl group, for example 2,6-di$C_{1-6}$alkylphenyl. In one example thereof, A is 2,6-dimethylphenyl.

In other embodiments, A is an optionally substituted 5-membered heteroaryl group. One example thereof is optionally substituted pyrazole, for example, optionally substituted 1H-pyrazol-4-yl. Some exemplary optional substitution includes 3,5- or 1,3,5-$C_{1-6}$alkyl substitution, for example 3,5-dimethyl-1H-pyrazol-4-yl or 1,3,5-dimethyl-1H-pyrazol-4-yl.

In certain embodiments of the disclosure, $L_1$ and $L_2$ are independently selected from methylene, ethylene, propylene and butylene. Each linker group, $L_1$ and $L_2$, may be unsubstituted or independently substituted by one or more, same or different, substituents. Some exemplary substituents for $L_1$ and $L_2$ include $C_{1-6}$alkyl, such as methyl, ethyl and propyl (n- or i-) substituted or unsubstituted phenyl and substituted or unsubstituted 5-6-membered heteroaryl as described herein, such as substituted or unsubstituted pyridinyl, pyridazinyl, pyrimidinyl and pyrazinyl. In some examples $L_2$ (e.g. methylene) is substituted with a substituted or unsubstituted phenyl or substituted or unsubstituted 5-6-membered heteroaryl group as described herein, such as substituted or unsubstituted pyridinyl, pyridazinyl, pyrimidinyl and pyrazinyl. In certain examples, $L_1$ is unsubstituted and $L_2$ is unsubstituted. In other embodiments $L_1$ is unsubstituted and $L_2$ is substituted. In other embodiments $L_1$ is substituted and $L_2$ is substituted. In other embodiments $L_1$ is substituted and $L_2$ is unsubstituted. In further examples $L_1$ is unsubstituted ethylene or propylene. In still further examples, $L_1$ is unsubstituted propylene. In still further examples $L_1$ is unsubstituted ethylene or propylene and $L_2$ is unsubstituted methylene. In other examples $L_1$ is unsubstituted ethylene or propylene, such as unsubstituted propylene, and $L_2$ is substituted methylene, for example methylene substituted with substituted or unsubstituted phenyl, or substituted or unsubstituted 5-6-membered heteroaryl as described herein, such as substituted or unsubstituted pyridinyl, pyridazinyl, pyrimidinyl and pyrazinyl.

In some embodiments, B is optionally substituted phenyl, or optionally substituted 6-membered heteroaryl, such as optionally substituted pyridyl (e.g. optionally substituted 2-, 3- or 4-pyridyl) or optionally substituted 4- or 5-pyrimidyl. In some further examples, where valencies allow, B may bear one substituent ortho-, or meta- or para- to the carbon attached to $L_2$. In further embodiments, where valencies allow, B may bear two substituents, for example, ortho-, ortho; ortho-,meta-; ortho-, para-; meta-, meta-or meta-, para- to the carbon attached to $L_2$. In some embodiments, where valencies allow, B may bear 3 substituents. In some embodiments, when B is optionally substituted phenyl, B may bear one substituent ortho-, or meta- or para- to the carbon attached to $L_2$; or two substituents, for example, ortho-, ortho; ortho-,meta-; ortho-, para-; meta-, meta-or meta-, para- to the carbon attached to $L_2$.

In some embodiments:
A and B are independently selected from optionally substituted phenyl and 6-membered heteroaryl, e.g. both A and B are optionally substituted phenyl, or any other combination as described herein, wherein the nature and number of optional substituents are as described herein, or
A is an optionally substituted 5-membered heteroaryl group, and B is optionally substituted phenyl or optionally substituted 6-membered heteroaryl group, such as 2-, 3-, or 4-pyridyl, wherein the nature and number of optional substituents are as described herein; and
$L_1$ and $L_2$ are independently selected from methylene, ethylene, propylene and butylene, wherein, $L_1$ and $L_2$, may be unsubstituted or independently substituted by one or more, same or different, said optional substituents as described herein.

In still further embodiments, A is a 2,6-disubstituted phenyl group, such as 2,6-di$C_{1-6}$alkylphenyl, for example, A is 2,6-dimethylphenyl. In still further examples A is 2,6-dimethylphenyl and $L_1$ is unsubstituted propylene. In still further examples of A, or the combination of A and $L_1$, B is optionally substituted phenyl, said optional substitution as described herein, such as one or two optional substituents. In yet further embodiments of A and combinations of A and $L_1$, and A, $L_1$ and B, $L_2$ is methylene, which may be unsubstituted or substituted by an optional substituent as described herein.

Other embodiments include any combinations of any embodiments of A, B, $L_1$ and $L_2$ as described herein, wherein R is hydrogen. Still other embodiments include any combination of any embodiments of A, B, $L_1$ and $L_2$ as described herein wherein R is a $C_{1-6}$alkyl group.

The compounds of the disclosure may be prepared in accordance with, or analogous to, the methods described herein or any other methods known in the art of synthetic organic chemistry.

In some embodiments, compounds of the disclosure may be prepared by reacting an appropriate aryloxyamine A-O-$L_1$-$NH_2$, (or suitable salt, for example as the hydrochloride salt thereof) with a phenolic aldehyde in the presence of a reducing agent (e.g. $NaBH_4$, $NaCNBH_3$, $NaBH(AcO)_3$), such as described in *J. Org. Chem.*, 1996, 61, 3849-3862.

It will be recognised that during the processes for the preparation of compounds contemplated by the present disclosure, it may be necessary or desirable to protect certain functional groups which may be reactive or sensitive to the reaction or transformation conditions undertaken (e.g. OH (including diols), $NH_2$, $CO_2H$, SH, C=O). Suitable protecting groups for such functional groups are known in the art and may be used in accordance with standard practice. As used herein, the term "protecting group", refers to an introduced functionality that temporarily renders a particular functional group inactive under certain conditions. Such protecting groups and methods for their installation and subsequent removal at an appropriate stage are described in *Protective Groups in Organic Chemistry*, $3^{rd}$ Edition, T. W. Greene and P. G. Wutz, John Wiley and Sons, 1999, the entire contents of which are incorporated herein by reference. Exemplary forms of protected groups include:

for amino ($NH_2$)—carbamates (such as Cbz, Boc, Fmoc), benzylamines, acetamides (e.g. acetamide, trifluoroacetamide), azides;

for carbonyl—acetals, ketals, dioxanes, dithianes, and hydrazones;

for hydroxy—ethers (e.g. alkyl ethers, alkoxylalkyl ethers, allyl ethers, silyl ethers, benzyl ethers, tetrahydropyranyl ethers), carboxylic acid esters, acetals (e.g. acetonide and benzylidene acetal);

for thio (SH)—ethers (e.g. alkyl ethers, benzyl ethers), esters for $CO_2H$—esters (e.g. alkyl esters, benzyl esters).

It will also be recognised that certain compounds of formula (I) may possess asymmetric centres and are therefore capable of existing in more than one stereoisomeric form, such as enantiomers and diastereomers. The disclosure thus also relates to optically active compounds and compounds in substantially pure isomeric form at one or more asymmetric centres, e.g., enantiomers having greater than about 90% ee, such as about 95% or 97% ee or greater than 99% ee, as well as mixtures, including racemic mixtures, thereof. Such isomers may be prepared by asymmetric synthesis, for example using chiral intermediates, enzymes, or mixtures may be resolved by conventional methods, e.g., chromatography, recrystallization or use of a resolving agent.

The compounds of the present disclosure may also be administered as prodrugs and thus the disclosure also contemplates prodrugs of formula (I). The term "prodrug" is used in its broadest sense and encompasses those derivatives that are converted in vivo, either enzymatically or hydrolytically, to the compounds of the disclosure. Such derivatives would readily occur to those skilled in the art, and include, for example, compounds where a free hydroxy or thiol group is converted into an ester, such as an acetate, an acylal, such as acetoxymethyl, or thioester; or where a free amino group is converted into an amide or imine. Procedures for modifying the compounds of the disclosure, for example to prepare ester, acylal, imine and amide prodrugs, are well known in the art and may include treatment of the compound with an appropriate carboxylic acid, anhydride or chloride in the presence of a suitable catalyst or base. Esters of carboxylic acid (carboxy) groups are also contemplated. Suitable esters $C_{1-6}$alkyl esters; $C_{1-6}$alkoxymethyl esters, for example methoxymethyl or ethoxymethyl; $C_{1-6}$alkanoyloxymethyl esters, for example, pivaloyloxymethyl; phthalidyl esters; $C_{3-8}$cycloalkoxycarbonyl$C_{1-6}$alkyl esters, for example, 1-cyclohexylcarbonyloxyethyl; 1,3-dioxolen-2-onylmethyl esters, for example, 5-methyl-1,3-dioxolen-2-onylmethyl; and $C_{1-6}$alkoxycarbonyloxyethyl esters, for example, 1-methoxycarbonyloxyethyl. Prodrugs of amino functional groups include amides (see, for example, *Adv. BioSci.*, 1979, 20, 369, Kyncl, J. et al), enamines (see, for example, *J. Pharm. Sci.*, 1971, 60, 1810, Caldwell, H. et al), Schiff bases (see, for example, U.S. Pat. No. 2,923,661 and *Antimicrob. Agents Chemother.*, 1981, 19, 1004, Smyth, R. et al), oxazolidines (see, for example, *J. Pharm. Sci*, 1983, 72, 1294, Johansen, M. et al), Mannich bases (see, for example, *J. Pharm. Sci.* 1980, 69, 44, Bundgaard, H. et al and *J. Am. Chem. Soc.*, 1959, 81, 1198, Gottstein, W. et al), hydroxymethyl derivatives (see, for example, *J. Pharm. Sci*, 1981, 70, 855, Bansal, P. et al) and N-(acyloxy)alkyl derivatives and carbamates (see, for example, *J. Med. Chem.*, 1980, 23, 469, Bodor, N. et al, *J. Med. Chem.*, 1984, 27, 1037, Firestone, R. et al, *J. Med. Chem.*, 1967, 10, 960, Kreiger, M. et al, U.S. Pat. No. 5,684,018 and *J. Med. Chem.*, 1988, 31, 318-322, Alexander, J. et al). Esters of phosphoric acids such as phosphate esters of the phenolic hydroxy are also contemplated (see, for example, Mantyla et al, *J. Med. Chem.*, 2004, 47:188-195). Amino acids may also be used to form amino acid esters with hydroxyl groups such as phenolic or aliphatic hydroxyl groups (see for example U.S. Pat. Nos. 6,362,234, 7,550,506 and *Pharm Res.* 1998, 15(8):1154-9). Other conventional procedures for the selection and preparation of suitable prodrugs are known in the art and are described, for example, in WO 00/23419; *Design of Prodrugs*, H. Bundgaard, Ed., Elsevier Science Publishers, 1985; *Methods in Enzymology*, 42: 309-396, K. Widder, Ed, Academic Press, 1985; *A Textbook of Drug Design and Development*, Krogsgaard-Larsen and H. Bundgaard, Eds, Chapter 5, p 113-191 (1991); *Advanced Drug Delivery Reviews*, 8; 1-38 (1992); *Journal of Pharmaceutical Sciences*, 77;285 (1988), H. Bundgaard, et al; *Chem Pharm Bull*, 32692 (1984), N. Kakeya et al and *The Organic Chemistry of Drug Design and Drug Action*, Chapter 8, pp 352-401, Academic press, Inc., 1992.

Suitable pharmaceutically acceptable salts of compounds of formula (I) include, but are not limited to salts of pharmaceutically acceptable inorganic acids such as hydrochloric, sulphuric, phosphoric nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benzenesulphonic, salicyclic, sulphanilic, aspartic, glutamic, edetic, stearic, palmitic, oleic, lauric, pantothenic, tannic, ascorbic, fendizoic, 4-4'-methylenebis-3-hydroxy-2-naphthoic acid, o-(p-hydroxybenzoyl)benzoic, 4'-4"-dihydroxytriphenylmethane-2-carboxylic acid and valeric acids. Base salts include, but are not limited to, those formed with pharmaceutically acceptable cations, such as sodium, potassium, lithium, calcium, magnesium, ammonium and alkylammonium. Basic nitrogen-containing groups may be quaternised with such agents as lower alkyl halide, such as methyl, ethyl, propyl, and butyl chlorides, bromides and iodides or dialkyl sulfates such as dimethyl and diethyl sulfate.

The compounds of the disclosure may be in crystalline form either as the free compounds or as solvates and it is intended that both forms are within the scope of the present disclosure. The term "solvate" refers to a complex or aggregate formed by one or more molecules of a solute, i.e. compounds contemplated by the disclosure, and one or more molecules of a solvent. Suitable solvents are well understood in the art and include for example, of water, i.e. to form hydrates (e.g. mono-, di and tri-hydrates), and common organic solvents such as alcohols (methanol, ethanol, isopropanol) and acetic acid. Methods of solvation are generally known within the art, for example, recrystallization from an appropriate solvent.

In some embodiments, one or more compounds may block or inhibit any one or more $Na_v$ channel subtypes selected from $Na_v$ 1.1, $Na_v$1.2, $Na_v$1.3, $Na_v$1.4, $Na_v$1.5, $Na_v$1.6, $Na_v$1.7, $Na_v$1.8 or $Na_v$1.9. In further embodiments, one or more compounds may block or inhibit any one or more $Na_v$ channel subtypes localised on the peripheral and/or central nervous system, such as any one of $Na_v$ 1.1, $Na_v$1.2, $Na_v$1.3, $Na_v$1.6, $Na_v$1.7, $Na_v$1.8 or $Na_v$1.9.

One or more compounds may inhibit one or more such channel subtypes and/or be selective in their level of inhibition for one or more channels over one or more other channels and/or one conformational state over another, that is to say, the compound(s) may have a greater inhibitory activity for one channel subtype over another.

In some embodiments, the compounds of the disclosure inhibit the $Na_v$1.2 channel. Such compounds may be useful in the treatment of diseases and disorders which are mediated by $Na_v$1.2 activity, that is to say, in which excessive, unwanted or undesirable $Na_v$1.2 activity is implicated, and which may be responsive to inhibition of $Na_v$1.2 activity. Such diseases and disorders include those whose aetiologies and/or resulting symptoms have an excessive or undesirable $Na_v$1.2 activity component, and include epileptic disorders, such as those described herein, particularly seizures associated with epileptic disorders, and neuropathic pain.

In some embodiments, the compounds of the disclosure inhibit the $Na_v1.6$ channel. Such compounds may be useful in the treatment of diseases and disorders which are mediated by $Na_v1.6$ activity, that is to say, in which excessive or undesirable $Na_v1.6$ activity is implicated, and which may be responsive to inhibition of $Na_v1.6$ activity. Such disorders include those whose aetiologies and/or resulting symptoms have an excessive or undesirable $Na_v1.6$ activity component, and include epileptic disorders, such as those described herein, particularly seizures associated with epileptic disorders.

In some embodiments, by virtue of selective affinity for one or more $Na_v$ channel subtypes over one or more other $Na_v$ channel subtypes, some compounds of the disclosure may potentially afford drugs with greater potency or reduced side effects. In some embodiments, some compounds may have selective affinity for $Na_v1.2$ channels over other $Na_v$ channel subtypes, such as $Na_v1.6$ channels e.g. their inhibitory activity is greater for $Na_v1.2$ channels than, say $Na_v1.6$ channels. In other embodiments some compounds may have selective affinity for $Na_v1.6$ channels over other $Na_v$ channel subtypes, such as $Na_v 1.2$ channels e.g. their inhibitory activity is greaterfor $Na_v1.6$ channels than, say $Na_v1.2$ channels Without limiting the disclosure by theory, a compound of the disclosure may block or inhibit channel activity by binding or otherwise interacting or associating with the sodium channel in any one or more of the conformational states (resting (tonic), activated (open) and inactivated (closed)). In some embodiments, the compound may bind or interact or associate preferentially or selectively with one conformational state over another or two conformational states over another. In some embodiments the compound has preferential or selective affinity for, that is to say, binds or otherwise interacts or associates with, the sodium channel in the resting state. In some embodiments the compound has preferential or selective affinity for, that is to say, binds or otherwise interacts or associates with, the sodium channel in the activated state. In some embodiments, the compound has preferential or selective affinity for, that is to say, binds or otherwise interacts or associates with, the sodium channel in the inactivated state. For example, in some embodiments, one or more compounds may bind with the resting state and/or activated state and/or inactivated state of the $Na_v1.2$ subtype. In some embodiments or more compounds may bind with the resting state and/or activated state and/or inactivated state of the $Na_v1.6$ subtype. Methods for determining such binding/interactions are known in the art (see, for example, the Examples described herein, and methods described in Ilyin, V. I. et al, *British Journal of Pharmacology*, 2005, 144, 801-812 and Ilyin, V. I. et al, *The Journal of Pharmacology and Experimental Therapeutics*, 2006, 318, 1083-1093).

As used herein, "inhibit" and "block", and associated terms such as "inhibiting" and "blocking" etc, may be used interchangeably, and when used with reference to the compounds of the disclosure includes an association or interaction of the compound with the sodium channel or other endogenous molecule such that transition from one conformational state to another is prevented, restricted, slowed, delayed or otherwise compromised. Thus, inhibition or blocking may be complete or partial.

Without limiting the disclosure by theory, the association or interaction may be direct, such as where the compound binds to or is associated directly with one or more subunits of the sodium channel, or the association or interaction may be indirect, such as where the compound binds to or is associated with some other endogenous molecule, for example, whereby it causes a conformational change in one or more subunits of the sodium channel Subjects to be treated in accordance with the disclosure include mammalian subjects: humans, primates, livestock animals (including cows, horses, sheep, pigs and goats), companion animals (including dogs, cats, rabbits, guinea pigs), and captive wild animals. Laboratory animals such as rabbits, mice, rats, guinea pigs and hamsters are also contemplated as they may provide a convenient test system. Non-mammalian species such as birds, amphibians and fish may also be contemplated in certain embodiments of the disclosure. Particularly contemplated subjects are human subjects.

The compounds of the disclosure are administered in an amount and in accordance with a regimen effective to achieve the desired outcome (e.g. full or partial inhibition of sodium channel activity or treatment or prevention of the disorder). An effective amount is intended to include an amount which, when administered according to the desired dosing regimen, at least partially attains the desired treatment or prevention effect.

The compounds of the disclosure may find utility in the treatment or prevention of a disease or disorder in which $Na_v$ channel activity is implicated, such as epilepsy and seizures, multiple sclerosis, migraine, cancers, such as breast, ovary, prostate, lung and cervical cancer, including metastatic forms, and neuropathic pain.

As used herein, "treatment" includes one or more of: alleviating, eliminating or reducing the frequency and/or severity of one or more symptoms of, inhibiting or delaying the progression of, or halting or reversing (partially or altogether) the onset or progression of the particular disease or disorder, and/or one or more symptoms being treated.

Treatment of seizures associated with epileptic disorders (epileptic seizures) may include any one or more of: reduction in number of and/or frequency of seizures over a period of time, reduction in severity and reduction in duration of the seizure. Seizures that may be treated by the compounds disclosed herein include partial or focal seizures or generalized seizures. In further embodiments, the seizures to be treated are associated with myoclonic epilepsy of infancy (SMEI), generalized epilepsy with febrile seizures plus (GEFS+), simple febrile seizures, benign familial infantile seizures (BFIS), or benign familial neonatal-infantile seizures (BFNIS).

Treatment of neuropathic pain may include the amelioration or reduction in severity and/or or frequency of one or more sensory symptoms, including burning, tingling, numbness, or shooting pain, felt by a patient. In human patients this may be determined, for example, by means of a pain assessment scale such as the Neuropathic Pain Scale (NPS) or Neuropathic Pain Questionnaire (NPQ).

Treatment of migraine may include the amelioration or reduction in severity and/or or frequency of one or more symptoms. In human patients this may be determined, for example, by means of a pain assessment scale such as the migraine disability assessment scale (MIDAS).

Suitable dosage amounts and dosing regimens can be determined by the attending physician and may depend on the particular condition being treated, the severity of the condition as well as the general age, health and weight of the subject. Suitable dosage amounts may be administered as unit or daily dosages. Unit or daily dosages may lie in the range of from 1 µg to 1 g of compound, salt, solvate or prodrug, for example, 1 µg-1 mg, 1 mg-2.5 mg, 2.5 mg-5 mg, 7.5 mg-10 mg, 15 mg-25 mg, 25 mg-50 mg, 50 mg-7 mg 50 mg-100 mg, 100 mg-500 mg, 500 mg-750 mg or 750 mg-1000 mg, or anywhere between these exemplary ranges. Any of these dosages may be administered once, or multiple times daily, or one or more times weekly, fortnightly or monthly.

The active ingredient may be administered in a single dose or a series of doses. While it is possible for the active ingredient to be administered alone, it is preferable to present it as a composition, preferably as a pharmaceutical composition, with one or more pharmaceutically acceptable additives. The present disclosure also relates to the use of a compound of formula (I) or a pharmaceutically acceptable salt or prodrug thereof in the manufacture of a medicament for treating a disease or condition that is mediated by sodium channel activity.

The formulation of such compositions is well known to those skilled in the art, see for example, *Remington's Pharmaceutical Sciences*, 18$^{th}$ Edition, Mack Publishing, 1990. The composition may contain any suitable additive such as carriers, diluents or excipients. These include all conventional solvents, dispersion media, fillers, solid carriers, lubricants, disintergrants, coatings, antifungal and antibacterial agents, dermal penetration agents, surfactants, isotonic and absorption agents, colouring and pigment agents, flavours and the like. It will be understood that the compositions of the disclosure may also include other supplementary physiologically active agents.

The carrier must be pharmaceutically acceptable in the sense of being compatible with the other ingredients of the composition and not injurious to the subject. Compositions include those suitable for oral, rectal, nasal, topical (including dermal, buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier that constitutes one or more accessory ingredients. In general, the compositions may be prepared by uniformly and intimately bringing into association the active ingredient with liquid carriers or finely divided solid carriers or both, and then if necessary shaping the product.

Compositions of the present disclosure suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent), preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Devices for transdermal delivery, such as patches or plasters, may also be used to administer the compounds of the disclosure.

Compositions for rectal administration may be presented as a suppository with a suitable base comprising, for example, cocoa butter, glycerin, gelatin or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this disclosure may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Compounds and compositions of the disclosure may be administered to a patient or subject as teh sole therapeutic agent for the disease or disorder being treated, or may be administered in conjunction (either simultaneously or separately) with one or more other therapies for said disease or disorder.

The compounds of the disclosure may also be presented for use in veterinary compositions. These may be prepared by any suitable means known in the art. Examples of such compositions include those adapted for:

(a) oral administration, external application (e.g. drenches including aqueous and non-aqueous solutions or suspensions), tablets, boluses, powders, granules, pellets for admixture with feedstuffs, pastes for application to the tongue;
(b) parenteral administration, e.g. subcutaneous, intramuscular or intravenous injection as a sterile solution or suspension;
(c) topical application e.g. creams, ointments, gels, lotions, patches, plasters etc.

The disclosure will now be described with reference to the following examples that are provided for the purpose of illustrating certain embodiments of the disclosure and are not intended to limit the generality herein before described.

EXAMPLES

Example 1

General Methods for Reductive Amination
Method A1

A mixture of amine (1 eq.), aldehyde (1.2 eq.) and MeOH (5 mL/mmol amine) was stirred at room temperature under $N_2$ until no more amine was visible by thin-layer chromatography. $NaBH_4$ (1-2 eq.) was added and the mixture was stirred at r.t. for 30-60 min. The mixture was poured into sat. aq. $NaHCO_3$ and extracted with $Et_2O$ or EtOAc (3 times). The combined organic extracts were dried ($MgSO_4$), filtered, and the crude mixture purified according to Protocol A or B (below) to obtain products as their pure hydrochloride salts (see below).

Method A2

Where imine formation did not occur at room temperature in MeOH according to Method A1 as assessed by thin-layer chromatography, the reaction was instead conducted in EtOH at reflux. Upon consumption of amine, the reaction mixture was cooled to r.t. prior to $NaBH_4$ addition as per Method A1.

Method B

A mixture of amine (1 eq.), aldehyde (1.2 eq.) and 1,2-dichloroethane (5-10 mL/mmol amine) was stirred at room temperature under $N_2$ for 1 h. $NaBH(OAc)_3$ (1.4 eq.) was added and the mixture was stirred for 2-4 h then poured into sat. aq. $NaHCO_3$ and extracted with EtOAc. The organic phase was washed sequentially with sat. aq. $NaHCO_3$, $H_2O$, then brine, dried ($MgSO_4$), filtered, and the crude solution of product treated in one of two ways to obtain products as their pure hydrochloride salts (see below). Note on Method B—Owing to the tendency for this reaction to give tertiary amine products as well as the desired hydrochloride salts, the crude material was preferably purified using Purification Method B.

Purification Protocols
Protocol A

For reactions where very little starting amine remained the organic extract was treated with 1 M HCl in MeOH affording a crystalline precipitate that was collected by vacuum filtration. In cases where crystals did not form, mixtures were evaporated and crystallized from one of $MeOH/Et_2O$, $MeOH/H_2O$, $EtOH/H_2O$, $EtOH/THF$, $MeCN/H_2O$ or $MeOH/THF$, as noted. If necessary, compounds were purified by recrystallization using one of the aforementioned solvent mixtures.

Protocol B

The dried organic extract was concentrated in vacuo and pure free-base was purified by flash chromatography using either EtOAc/petroleum spirits (10 to 100% with 1-2% $Et_3N$) or $EtOAc/MeOH/H_2O/Et_3N$ (97:2:1:2 to 7:2:1:0.2). After evaporation of the eluent the remaining $Et_3N$ was removed by azeotroping with dichloromethane. The free base was converted to the hydrochloride salt by either dissolving in $Et_2O$ and adding 1 M HCl in MeOH or dissolving in MeOH and adding aq. HCl (either 1 M or 10 M). Where necessary compounds were crystallized or recrystallized from $MeOH/Et_2O$, $MeOH/H_2O$, $EtOH/H_2O$, $EtOH/THF$, $MeCN/H_2O$ or $MeOH/THF$, as noted.

Compound 504

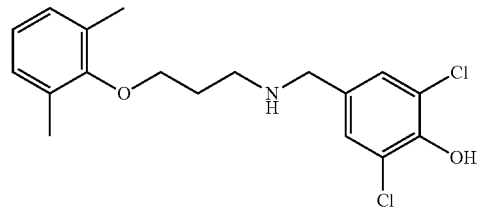 [SMILES: Cc1cccc(C)c1OCCCNCc1cc(Cl)c(O)c(Cl)c1]

2,6-Dichloro-4-((3-(2,6-dimethylphenoxy)propylamino)methyl)phenol (504). Method A1 applied to 3-(2,6-dimethylphenoxy)propylamine, followed by purification Protocol B ($MeOH/H_2O$) afforded the title compound (318 mg, 64%).
$^1$H NMR (400 MHz, $CD_3OD$) δ 2.19-2.24 (8H, m, 2×$CH_3$, $CH_2CH_2N$), 3.33-3.35 (2H, m, $CH_2N$), 3.87 (2H, t, J 5.9 Hz, $CH_2O$), 4.19 (2H, s, $ArCH_2N$), 6.89 (1H, t, J 7.5 Hz, Ar), 6.98-7.00 (2H, m, Ar), 7.53 (2H, s, Ar);
$^{13}$C NMR (100 MHz, $CD_3OD$) δ 16.41, 28.11, 46.36, 50.93, 69.93, 123.82, 123.84, 124.82, 125.25, 129.95, 131.47, 131.68, 151.98, 156.60;
HRMS (ESI$^+$): m/z 354.1027 [M+H]$^+$ (calcd. [$C_{18}H_{21}Cl_2NO_2$+H]$^+$ 354.1022).

Compound 518

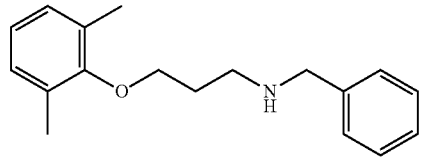 [SMILES: Cc1cccc(C)c1OCCCNCc1ccccc1]

N-Benzyl-3-(2,6-dimethylphenoxy)propan-1-amine (518). Method A1 applied to 3-(2,6-dimethylphenoxy)propylamine and benzaldehyde, followed by purification Protocol B ($MeOH/H_2O$) afforded the title compound (135 mg, 37%).
$^1$H NMR (500 MHz, $CD_3OD$) δ 2.16-2.22 (2H, m,$CH_2CH_2N$), 2.23 (6H, 2×$CH_3$), 3.34 (2H, t, J 6.4 Hz, $CH_2N$), 3.87 (2H, t, J 5.8 Hz, $CH_2O$), 4.26 (2H, s, $ArCH_2N$), 6.90 (1H, t, J 6.0 Hz, Ar), 7.00 (2H, m Ar), 7.45-7.53 (5H, m, Ar); $^{13}$C NMR (125 MHz, $CD_3OD$) δ 16.42, 28.12, 46.46, 52.42, 69.97, 125.26, 129.97, 130.33, 130.74, 131.06, 131.69, 132.51, 156.63; HRMS (ESI⁺): m/z 270.1857 [M+H]⁺ (calcd. [C$_{18}$H$_{23}$NO+H]⁺ 270.1857).

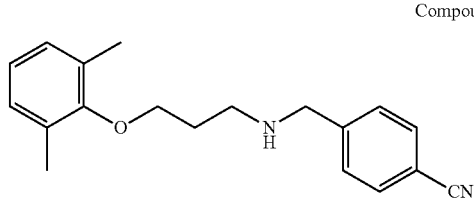

Compound 519

4-((3-(2,6-Dimethylphenoxy)propylamino)methyl)benzonitrile (519). Method A1 applied to 3-(2,6-dimethylphenoxy)propylamine and 4-cyanobenzaldehyde, followed by purification Protocol A (MeOH/Et$_2$O) afforded the title compound (117 mg, 77%).
¹H NMR (500 MHz, CD$_3$OD) δ 2.16-2.24 (8H, m, 2×CH$_3$, CH$_2$CH$_2$N), 3.35-3.39 (2H, m, CH$_2$N), 3.86 (2H, t, J 5.9 Hz, CH$_2$O), 4.35 (2H, s, ArCH$_2$N), 6.88 (1H, dd, J 8.1, 6.8 Hz, Ar), 6.97 (2H, d, J 7.7 Hz, Ar), 7.68-7.70 (2H, m, Ar), 7.82-7.85 (2H, m, Ar);
¹³C NMR (125 MHz, CD$_3$OD) δ 16.41, 28.24, 46.91, 51.75, 69.88, 114.60, 119.02, 125.30, 129.99, 131.68, 131.97, 134.06, 137.94, 156.63;
HRMS (ESI⁺): m/z 295.1804 [M+H]⁺ (calcd. [C$_{19}$H$_{22}$N$_2$O+H]⁺ 295.1805).

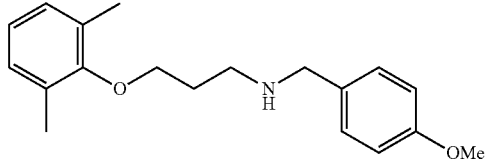 [SMILES: COc1ccc(CNCCCOc2c(C)cccc2C)cc1]

Compound 520

3-(2,6-Dimethylphenoxy)-N-(4-methoxybenzyl)propan-1-amine (520). Method A1 applied to 3-(2,6-dimethylphenoxy)propylamine and 4-methoxybenzaldehyde, followed by purification Protocol B (MeOH/H$_2$O) afforded the title compound (336 mg, 78%).
¹H NMR (500 MHz, CD$_3$OD) δ 2.15-2.22 (2H, m, CH$_2$CH$_2$N), 2.24 (3H, s, 2×CH$_3$), 3.30-3.35 (2H, m, CH$_2$N), 3.82 (3H, s, OCH$_3$), 3.87 (2H, t, J 5.8 Hz, CH$_2$O), 4.20 (2H, s, ArCH$_2$N), 6.90 (1H, t, J 7.8 Hz, Ar), 6.98-7.04 (4H, m, Ar), 7.42-7.46 (2H, m, Ar);
¹³C NMR (125 MHz, CD$_3$OD) δ 16.45, 28.07, 46.37, 49.85, 55.90, 69.98, 116.29, 116.42, 123.05, 125.20, 129.93, 131.35, 131.68, 133.78, 156.61, 161.64;
HRMS (ESI⁺): m/z 300.1964 [M+H]⁺ (calcd. [C$_{19}$H$_{25}$NO$_2$+H]⁺ 300.1963).

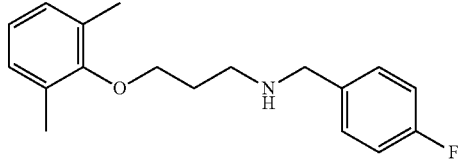 [SMILES: Cc1cccc(C)c1OCCCNCc1ccc(F)cc1]

Compound 521

3-(2,6-Dimethylphenoxy)-N-(4-fluorobenzyl)propan-1-amine (521). Method A1 applied to 3-(2,6-dimethylphenoxy)propylamine and 4-fluorobenzaldehyde, followed by purification Protocol B (MeOH/H$_2$O) afforded the title compound (239 mg, 62%).
¹H NMR (500 MHz, CD$_3$OD) δ 2.21-2.28 (8H, m, 2×CH$_3$, CH$_2$CH$_2$N), 3.36 (2H, t, J 7.9 Hz, CH$_2$N), 3.87 (2H, t, J 5.8 Hz, CH$_2$O), 4.29 (2H, s, ArCH$_2$N), 6.90 (1H, t, J 7.4 Hz, Ar), 6.99 (2H, d, J 7.4 Hz, Ar), 7.21 (2H, t, J 8.6 Hz, Ar), 7.61 (2H, dd, J 8.2, 5.4 Hz, Ar);
¹³C NMR (125 MHz, CD$_3$OD) δ 16.43, 28.14, 46.42, 51.57, 69.94, 116.99, 117.16, 125.24, 128.65, 128.67, 129.96, 131.69, 133.46, 133.53, 156.64, 163.85, 165.82;
HRMS (ESI⁺): m/z 288.1765 [M+H]⁺ (calcd. [C$_{18}$H$_{22}$FNO+H]⁺ 288.1763).

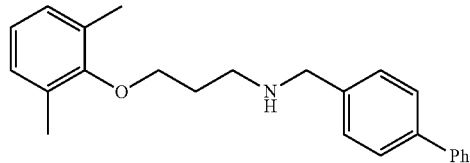

Compound 522

N-(Biphenyl-4-ylmethyl)-3-(2,6-dimethylphenoxy)propan-1-amine (522). Method B applied to 3-(2,6-dimethylphenoxy)propylamine and 4-phenylbenzaldehyde, followed by purification Protocol B (MeOH/Et$_2$O) afforded the title compound (206 mg, 61%).
¹H NMR (500 MHz, CD$_3$OD) δ 2.25 (8H, s, 2×CH$_3$, CH$_2$CH$_2$N), 3.37-3.41 (2H, m, CH$_2$N), 3.89 (2H, t, J 5.9 Hz, CH$_2$O), 4.33 (2H, s, ArCH$_2$N), 6.90 (1H, t, J 7.5 Hz, Ar), 7.00 (2H, d, J 7.5 Hz, Ar), 7.37 (1H, t, J 7.4 Hz, Ar), 7.46 (2H, t, J 7.7 Hz, Ar), 7.61 (2H, d, J 8.2 Hz, Ar), 7.64 (2H, d, J 7.2 Hz, Ar), 7.74 (2H, d, J 8.2 Hz, Ar);
¹³C NMR (125 MHz, CDCl$_3$; spectrum of free base) δ 6.37, 30.89, 46.90, 53.95, 70.71, 123.83, 127.16, 127.27, 128.73, 128.84, 128.91, 130.98, 139.52, 140.05, 141.10, 156.01;
HRMS (ESI⁺): m/z 346.2165 [M+H]⁺ (calcd. [C$_{24}$H$_{27}$NO+H]⁺ 346.2165).

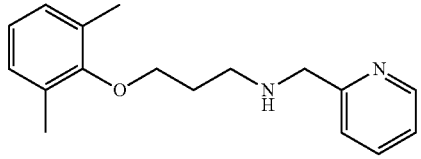

Compound 523

3-(2,6-Dimethylphenoxy)-N-(pyridin-2-ylmethyl)propan-1-amine (523). Method B applied to 3-(2,6-dimethylphenoxy)propylamine and 2-picolinaldehyde, followed by purification Protocol B (MeOH/Et$_2$O) afforded the title compound (127 mg, 47%).
¹H NMR (500 MHz, CD$_3$OD) δ 2.28 (6H, s, J 3.0 Hz, 2×CH$_3$), 2.28-2.34 (2H, m, CH$_2$CH$_2$N), 3.50-3.53 (2H, m, CH$_2$CH$_2$N), 3.93 (2H, t, J 5.9 Hz, CH$_2$O), 4.63 (2H, s, ArCH$_2$N), 6.91 (1H, t, J 7.5 Hz, Ar), 7.00-7.01 (2H, Ar), 7.80 (1H, ddd, J 7.6, 5.4, 0.8 Hz, Ar), 7.94 (1H, d, J 7.9 Hz, Ar), 8.30-8.33 (1H, td, J 7.8, 1.7 Hz, Ar), 8.82 (1H, m, Ar);

$^{13}$C NMR (100 MHz, CD$_3$OD) δ 16.48, 28.23, 47.46, 49.71, 69.93, 69.95, 69.96, 125.27, 127.60, 127.75, 129.96, 131.73, 145.04, 146.61, 149.10, 156.66;
HRMS (ESI$^+$): m/z 271.1805 [M+H]$^+$ (calcd. [C$_{17}$H$_{22}$N$_2$O+H]$^+$ 271.1805).

Compound 524

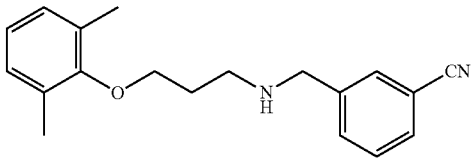

3-((3-(2,6-Dimethylphenoxy)propylamino)methyl)benzonitrile (524). Method A1 applied to 3-(2,6-dimethylphenoxy)propylamine and 3-cyanobenzaldehyde, followed by purification Protocol A (MeOH/Et$_2$O) afforded the title compound (77.1 mg, 62%).
$^1$H NMR (600 MHz, CD$_3$OD) δ 2.21-2.27 (8H, m, 2×CH$_3$, CH$_2$CH$_2$N), 3.38-3.41 (2H, m, CH$_2$N), 3.89 (2H, t, J 5.9 Hz, CH$_2$O), 4.37 (2H, s, ArCH$_2$N), 6.91 (1H, t, J 7.5 Hz, Ar), 7.00 (2H, d, J 7.2 Hz, Ar), 7.68 (1H, t, J 7.8 Hz, Ar), 7.84-7.88 (2H, m, Ar), 7.94 (1H, s, Ar);
$^{13}$C NMR (125 MHz, CD$_3$OD) δ 16.42, 28.19, 46.76, 51.39, 69.85, 114.36, 119.02, 125.28, 129.98, 131.46, 131.70, 134.33, 134.35, 135.85, 156.63;
HRMS (ESI$^+$): m/z 295.1804 [M+H]$^+$ (calcd. [C$_{19}$H$_{22}$N$_2$O+H]$^+$ 295.1805).

Compound 525

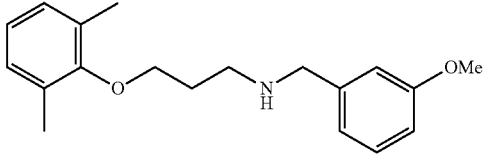 [SMILES: COc1cccc(CNCCCOc2c(C)cccc2C)c1]

3-(2,6-Dimethylphenoxy)-N-(3-methoxybenzyl)propan-1-amine (525). Method A1 applied to 3-(2,6-dimethylphenoxy)propylamine and 3-methoxybenzaldehyde, followed by purification Protocol B (MeOH/Et$_2$O) afforded the title compound (248 mg, 66%).
$^1$H NMR (500 MHz, CD$_3$OD) δ 2.19-2.22 (8H, m, 2×CH$_3$, CH$_2$CH$_2$N), 3.35 (2H, m, CH$_2$N), 3.83 (3H, s, OCH$_3$), 3.88 (2H, t, J 5.8 Hz, CH$_2$O), 4.25 (2H, s, ArCH$_2$N), 6.90 (1H, dd, J 7.9, 7.1 Hz, Ar), 6.99-7.04 (3H, m, Ar), 7.08-7.12 (2H, m, Ar), 7.39 (1H, t, J 7.9 Hz, Ar);
$^{13}$C NMR (100 MHz, CD$_3$OD) δ 16.45, 28.07, 46.37, 49.85, 55.90, 69.98, 116.29, 116.42, 123.05, 125.20, 129.93, 131.35, 131.68, 133.78, 156.61, 161.64;
HRMS (ESI$^+$): m/z 300.1976 [M+H]$^+$ (calcd. [C$_{19}$H$_{25}$NO$_2$+H]$^+$ 300.1958).

Compound 526

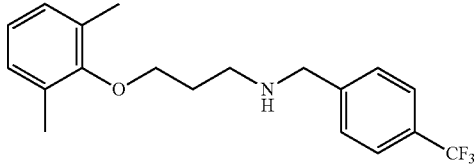 [SMILES: Cc1cccc(C)c1OCCCNCc1ccc(C(F)(F)F)cc1]

3-(2,6-Dimethylphenoxy)-N-(4-trifluoromethyl)benzyl)propan-1-amine (526). Method B applied to 3-(2,6-dimethylphenoxy)propylamine and 4-trifluoromethylbenzaldehyde, followed by purification Protocol B (MeOH/Et$_2$O) afforded the title compound (206 mg, 61%).
$^1$H NMR (400 MHz, CDCl$_3$) δ 2.02 (2H, quintet, J 6.4 Hz, CH$_2$CH$_2$CH$_2$), 2.26 (6H, s, s, 2×CH$_3$), 2.91 (2H, t, J 6.8 Hz, CH$_2$CH$_2$N), 3.85 (2H, t, J 6.1 Hz, CH$_2$N), 3.90 (2H, s, ArCH$_2$N), 6.92 (1H, dd, J 8.2 and 6.7 Hz, Ar), 7.00-7.02 (2H, Ar), 7.47 (2H, d, J 8.0 Hz, Ar), 7.59 (2H, d, J 8.0 Hz, Ar);
$^{13}$C NMR (100 MHz, CDCl$_3$) δ 16.28, 30.84, 46.94, 53.71, 70.61, 123.85, 124.38 (1 C, quartet, J 271.9 Hz, CF$_3$), 125.35 (2 C, quartet, J 3.8 Hz, 2×CCCF$_3$), 128.38, 128.90, 129.22 (1 C, quartet, J 32.3 Hz, CCF$_3$), 130.91, 144.74, 155.92;
HRMS (ESI$^+$): m/z 338.1725 [M+H]$^+$ (calcd. [C$_{19}$H$_{22}$F$_3$NO+H]$^+$ 338.1726).

Compound 528

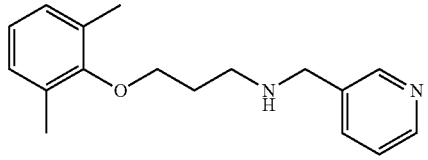

3-(2,6-Dimethylphenoxy)-N-(pyridin-3-ylmethyl)propan-1-amine (528). Method B applied to 3-(2,6-dimethylphenoxy)propylamine and 3-picolinaldehyde, followed by purification Protocol B (MeOH/Et$_2$O) afforded the title compound (99.6 mg, 66%).
$^1$H NMR (400 MHz, CD$_3$OD) δ 2.27 (6H, s, 2×CH$_3$), 2.28-2.35 (2H, m, CH$_2$CH$_2$N), 3.51 (2H, m, CH$_2$N), 3.91 (2H, t, J 6.0 Hz, CH$_2$O), 4.64 (2H, s, ArCH$_2$N), 6.90 (1H, dd, J 8.1, 6.8 Hz, Ar), 6.99 (2H, d, J 7.6 Hz, Ar), 8.23 (1H, dd, J 8.1, 5.8 Hz, Ar), 8.93-9.00 (2H, Ar), 9.23 (1H, d, J 1.5 Hz, Ar);
$^{13}$C NMR (100 MHz, CD$_3$OD) δ 16.49, 28.30, 47.22, 48.45, 69.77, 125.23, 128.90, 129.94, 131.72, 133.42, 143.73, 144.63, 149.80, 156.67;
HRMS (ESI$^+$): m/z 271.1805 [M+H]$^+$ (calcd. [C$_{17}$H$_{22}$N$_2$O+H]$^+$ 271.1805).

Compound 530

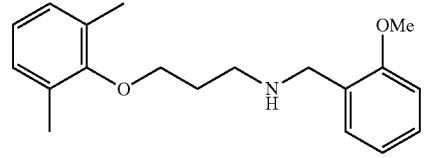 [SMILES: COc1ccccc1CNCCCOc1c(C)cccc1C]

3-(2,6-Dimethylphenoxy)-N-(2-methoxybenzyl)propan-1-amine (530). Method A1 applied to 3-(2,6-dimethylphenoxy)propylamine and 2-methoxybenzaldehyde, followed by purification Protocol B (MeOH/Et$_2$O) afforded the title compound (102.8 mg, 47%).
$^1$H NMR (500 MHz, CD$_3$OD) δ 2.20-2.25 (8H, m, 2×CH$_3$, CH$_2$CH$_2$N), 3.37 (2H, t, J 7.4 Hz, CH$_2$N), 3.82 (3H, s, OCH$_3$), 3.91 (2H, t, J 5.8 Hz, CH$_2$O), 4.29 (2H, s, ArCH$_2$N)), 6.92 (1H, t, J 7.5 Hz, Ar), 7.01-7.10 (4H, m, Ar), 7.41-7.48 (2H, m, Ar);

$^{13}$C NMR (125 MHz, CD$_3$OD) δ 16.42, 27.78, 46.92, 48.31, 56.11, 70.65, 112.12, 120.38, 122.11, 125.42, 130.04, 131.70, 132.77, 132.78, 156.49, 159.37;
LRMS (ESI$^+$): m/z 300.1969 [M+H]$^+$ (calcd. [C$_{19}$H$_{25}$NO$_2$+H]$^+$ 300.1958).

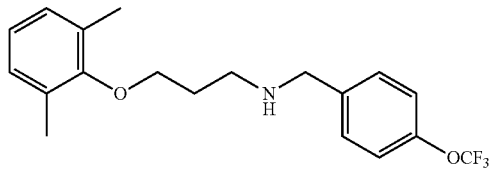 [SMILES: Cc1cccc(C)c1OCCCNCc1ccc(OC(F)(F)F)cc1]

Compound 531

3-(2,6-Dimethylphenoxy)-N-(4-(trifluoromethoxy)benzyl)propan-1-amine (531). Method A1 applied to 3-(2,6-dimethylphenoxy)propylamine and 4-methoxylbenzaldehyde, followed by purification Protocol A (MeOH/H$_2$O) afforded the title compound (157 mg, 72%).
$^1$H NMR (500 MHz, CD$_3$OD) δ 2.22-2.26 (8H, m, 2×CH$_3$, CH$_2$CH$_2$N), 3.37-3.40 (2H, m, CH$_2$N), 3.88 (2H, t, J 5.9 Hz, CH$_2$O), 4.33 (2H, s, ArCH$_2$N), 6.90 (1H, t, J 7.5 Hz, Ar), 7.00 (2H, d, J 7.4 Hz, Ar), 7.39-7.41 (2H, m, Ar), 7.66-7.68 (2H, m, Ar);
$^{13}$C NMR (125 MHz, CD$_3$OD) δ 16.42, 28.16, 46.61, 51.47, 69.92, 120.84 (1C, q, J 256.1 Hz, CF$_3$), 122.68, 125.27, 129.98, 131.70, 131.73, 133.24, 151.34, 156.65;
HRMS (ESI$^+$): m/z 354.1675 [M+H]$^+$ (calcd. [C$_{19}$H$_{22}$F$_3$NO$_2$+H]$^+$ 354.1675).

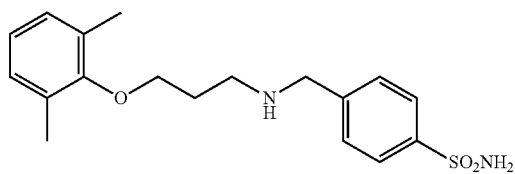

Compound 532

4-((3-(2,6-Dimethylphenoxy)propylamino)methyl)benzenesulfonamide (532). Method A1 applied to 3-(2,6-dimethylphenoxy)propylamine and 4-aminosulfonylbenzaldehyde, followed by purification Protocol B (MeOH/H$_2$O) afforded the title compound (277 mg, 62%).
$^1$H NMR (500 MHz, CD$_3$OD) δ 2.27-2.37 (8H, m, 2×CH$_3$, CH$_2$CH$_2$N), 3.40 (2H, t, J 8.0 Hz, CH$_2$N), 3.89 (2H, t, J 6.0 Hz, CH$_2$O), 4.38 (2H, s, ArCH$_2$N), 6.90 (1H, t, J 7.5 Hz, Ar), 7.00 (2H, d, J 7.5 Hz), 7.74 (2H, d, J 8.0 Hz, Ar), 8.00 (2H, d, J 8.0 Hz, Ar);
$^{13}$C NMR (125 MHz, CD$_3$OD) δ 16.42, 28.19, 46.78, 51.66, 69.90, 125.28, 127.96, 129.98, 131.69, 136.64, 146.37, 156.62;
HRMS (ESI$^+$): m/z 349.1588 [M+H]$^+$ (calcd. [C$_{18}$H$_{24}$N$_2$O$_3$S+H]$^+$ 349.1585).

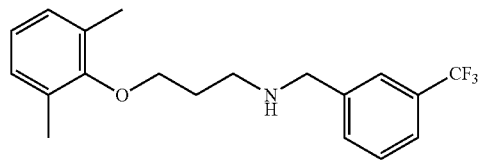

Compound 533

3-(2,6-Dimethylphenoxy)-N-(3-(trifluoromethyl)benzyl)propan-1-amine (533). Method B applied to 3-(2,6-dimethylphenoxy)propylamine and 3-trifluoromethylbenzaldehyde, followed by purification Protocol B (MeOH/Et$_2$O) afforded the title compound (304.0 mg, 72%).
$^1$H NMR (500 MHz, CDCl$_3$) δ 2.04 (2H, quintet, J 6.5 Hz, CH$_2$CH$_2$N), 2.29 (6H, s, 2×CH$_3$), 2.94 (2H, t, J 6.8, Hz CH$_2$N), 3.88 (2H, t, J 6.1 Hz, CH$_2$O), 3.91 (2H, ArCH$_2$N), 6.93 (1H, t, J 7.4 Hz, Ar), 7.02 (2H, d, J 7.4 Hz, Ar), 7.45 (1H, t, J 7.7 Hz, Ar), 7.55 (2H, dd, J 14.3, 7.7 Hz, Ar), 7.65 (1H, s, Ar);
$^{13}$C NMR (125 MHz, CDCl$_3$) δ 16.31, 30.86, 46.96, 53.78, 70.63, 123.87, 123.91 (1 C, quartet, J 3.8 Hz, CCCF$_3$), 124.36 (1 C, quartet, J 272.3 Hz, CF$_3$), 124.97 (1 C, quartet, J 3.8 Hz, CCCF$_3$), 128.91, 128.93, 130.83 (1 C, quartet, J 31.7 Hz, CCF$_3$), 130.95, 131.58, 131.59, 141.57, 155.98;
HRMS (ESI$^+$): m/z 338.1727 [M+H]$^+$ (calcd. [C$_{19}$H$_{22}$F$_3$NO+H]$^+$ 338.1726).

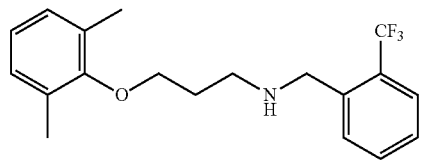

Compound 534

3-(2,6-Dimethylphenoxy)-N-(2-(trifluoromethyl)benzyl)propan-1-amine (534). Method B applied to 3-(2,6-dimethylphenoxy)propylamine and 2-trifluoromethylbenzaldehyde, followed by purification Protocol A (MeOH/H$_2$O) afforded the title compound (186.0 mg, 43%).
$^1$H NMR (400 MHz, CD$_3$OD) δ 2.24-2.31 (8H, m, 2×CH$_3$, CH$_2$CH$_2$N)), 3.47 (2H, dd, J 9.0, 6.9 Hz, CH$_2$N), 3.90 (2H, t, J 5.9 Hz, CH$_2$O), 4.50 (2H, s, ArCH$_2$N), 6.91 (1H, dd, J 8.1, 6.8 Hz, Ar), 6.99-7.01 (2H, m, Ar), 7.69 (1H, d, J 7.7 Hz, Ar), 7.78-7.82 (1H, m, Ar), 7.86 (2H, dd, J 7.7, 4.6 Hz, Ar);
$^{13}$C NMR (100 MHz, CDCl$_3$) δ 123.9, 124.6 (1 C, q, J 270 Hz, CF$_3$), (1 C, quartet, J 5.6 Hz, CCCF$_3$), 127.1, 128.4 (1 C, quartet, J 30.2 Hz, CCF$_3$), 130.6, 131.0, 132.1, 139.0, 156.0;
HRMS (ESI$^+$): m/z 338.1726 [M+H]$^+$ (calcd. [C$_{19}$H$_{22}$F$_3$NO+H]$^+$ 338.1726).

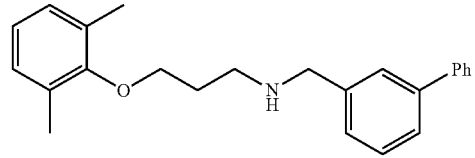

Compound 535

N-(Biphenyl-3-ylmethyl)-3-(2,6-dimethylphenoxy)propan-1-amine (535). Method B applied to 3-(2,6-dimethylphenoxy)propylamine and 3-phenylbenzaldehyde, followed by purification Protocol B (MeOH/H₂O) afforded the title compound (215.8 mg, 64%).

¹H NMR (400 MHz, CDCl₃) δ 2.09 (2H, quint, J 6.5 Hz, CH₂CH₂CH₂), 2.33 (6H, s, 2×CH₃), 3.00 (2H, t, J 6.9 Hz, CH₂N), 3.92 (2H, t, J 6.2 Hz, CH₂O), 3.96 (2H, s, ArCH₂N), 6.97 (1H, dd, J 8.1 and 6.7 Hz, Ar), 7.06 (2H, d, J 7.3 Hz, Ar), 7.38-7.56 (6H, m, Ar), 7.65-7.68 (3H, m, Ar);

¹³C NMR (100 MHz, CD₃OD) δ16.43, 28.09, 46.44, 52.34, 69.98, 125.25, 128.05, 128.85, 129.20, 129.75, 129.86, 129.96, 129.99, 130.83, 131.69, 133.08, 141.38, 143.52, 156.60;

HRMS (ESI⁺): m/z 346.2162 [M+H]⁺ (calcd. [C₂₄H₂₇NO+H]⁺ 346.2165).

Compound 536

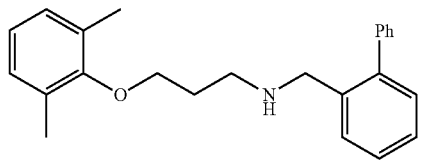

N-(Biphenyl-2-ylmethyl)-3-(2,6-dimethylphenoxy)propan-1-amine (536). Method B applied to 3-(2,6-dimethylphenoxy)propylamine and 2-phenylbenzaldehyde, followed by purification Protocol B (MeOH/H₂O) afforded the title compound (61.9 mg, 28%).

¹H NMR (500 MHz, CD₃OD) δ 2.01 (2H, m, CH₂CH₂CH₂), 2.17 (6H, s, 2×CH₃), 3.12 (2H, t, J 7.7 Hz, CH₂N), 3.76 (2H, t, J 5.8 Hz, CH₂O), 4.31 (2H, ArCH₂N), 6.90 (1H, dd, J 7.9 and 7.1 Hz, Ar), 6.99 (2H, d, J 7.5 Hz, Ar), 7.35-7.55 (8H, Ar), 7.65-7.68 (1H, Ar);

¹³C NMR (125 MHz, CDCl₃) δ 16.36, 30.85, 46.65, 51.56, 70.61, 123.75, 126.96, 127.13, 127.60, 128.24, 128.85, 129.19, 129.23, 130.17, 130.95, 137.79, 141.38, 141.89, 156.04;

HRMS (ESI⁺): m/z 346.2162 [M+H]⁺ (calcd. [C₂₄H₂₇NO+H]⁺ 346.2165).

Compound 538

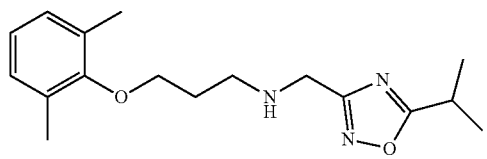

(5-Isopropyl-1,2,4-oxadiazol-3-yl)methyl tosylate. Sodium hydride in mineral oil (60%, 32.4 mg, 1.35 mmol) was added to a stirred solution of 5-isopropyl-1,2,4-oxadiazole-3-methanol (160 mg, 1.13 mmol), and dry THF (3 mL) at 0° C. under N₂ atmosphere. Tosyl chloride (249 mg, 1.35 mmol) was added at 0° C. and the mixture was stirred for 24 h. Additional sodium hydride (1.35 mmol) was added at 0° C. and the mixture was warmed to r.t. and stirred for 90 min. MeOH (1 mL) was added and the mixture was evaporated to dryness under reduced pressure. The crude residue was purified by flash chromatography to give pure (5-isopropyl-1,2,4-oxadiazol-3-yl)methyl tosylate (263 mg, 79%).

¹H NMR (400 MHz, CDCl₃) δ 1.34 (6H, d, J 7.0 Hz, CH(CH₃)₂), 2.44 (3H, s, ArCH₃), 3.16 (1H, septet, J 7.0 Hz, CH(CH₃)₂), 7.32-7.34 (2H, d, J 8.0 Hz, Ar), 7.81 (2H, d, J 8.3 Hz, Ar);

¹³C NMR (100 MHz, CDCl₃) δ 20.07, 21.78, 27.55, 61.53, 128.35, 129.99, 132.63, 145.38, 164.40, 185.10;

3-(2,6-Dimethylphenoxy)-N-((5-isopropyl-1,2,4-oxadiazol-3-yl)methyl)propan-1-amine (538). A mixture of 3-(2,6-dimethylphenoxy)propan-1-amine (210.0 mg, 1.16 mmol), (5-isopropyl-1,2,4-oxadiazol-3-yl)methyl tosylate (195.0 mg, 0.658 mmol), and dry THF (2 mL) was heated at reflux with stirring for 1.5 h. After cooling to r.t. and stirring for a further 3.5 h, triethylamine (456 μL, 3.29 mmol) was added and the mixture was heated at 50° C. for 17 h. The mixture was concentrated under reduced pressure and partitioned between Et₂O (10 mL) and sat. aq. NaHCO₃ (20 mL). The organic layer was separated and the aqueous phase extracted with Et₂O (2×10 mL). The combined organic extracts were sequentially washed with sat. aq. NaHCO₃, H₂O, brine, dried (MgSO4), filtered and concentrated under reduced pressure. Purification by protocol A (MeOH/Et₂O) gave the product (82.7 mg, 41%).

¹H NMR (400 MHz, CD₃OD) δ 1.38 (6H, d, J 6.8 Hz, CH(CH₃)₂), 2.19-2.27 (8H, m, 2×CH₃,CH₂CH₂N), 3.32 (1H, tt, J 7.0 Hz, CH(CH₃)₂), 3.49 (2H, t, J 7.8 Hz, CH₂O), 3.88 (2H, t, J 5.8 Hz, CH₂O), 4.49 (2H, s, ArCH₂N), 6.88 (1H, dd, J 8.1, 6.8 Hz, Ar), 6.97 (2H, d, J 7.5 Hz, Ar);

¹³C NMR (100 MHz, CD₃OD) δ 16.46, 20.29, 28.07, 28.68, 43.16, 47.37, 70.01, 70.02, 125.31, 129.98, 131.70, 156.63, 164.78, 187.10;

HRMS (ESI⁺): m/z 304.2018 [M+H]⁺ (calcd. [C₁₇H₂₅N₃O₂+H]⁺ 304.2020).

Compound 540

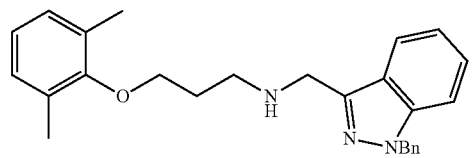

N-((1-Benzyl-1H-indazol-3-yl)methyl)-3-(2,6-dimethylphenoxy)propan-1-amine (540). Method A1 applied to 3-(2,6-dimethylphenoxy)propylamine and 1-benzyl-3-formyl-1H-indazole, followed by purification by Protocol A (MeOH/Et₂O) afforded the title compound (32.8 mg, 49%).

¹H NMR (400 MHz, CD₃OD) δ 2.22-2.27 (8H, m, 2×CH₃, CH₂CH₂N), 3.46-3.50 (2H, m, CH₂N), 3.87 (2H, t, J 5.8 Hz, CH₂O), 4.71 (2H, s, CH₂NH), 5.67 (2H, s, PhCH₂), 6.90 (1H, dd, J 8.2, 6.7 Hz, Ar), 6.99 (2H, d, J 7.4 Hz, Ar), 7.20-7.28 (6H, m, Ar), 7.46 (1H, ddd, J 8.4, 7.1, 1.1 Hz, Ar), 7.62 (1H, d, J 8.6 Hz, Ar), 7.90 (1H, dd, J 8.2, 0.8 Hz, Ar);

¹³C NMR (125 MHz, CD₃OD) δ 16.41, 28.06, 44.02, 46.81, 53.80, 70.17, 111.21, 120.38, 122.80, 123.92, 125.31, 128.44, 128.49, 128.89, 129.71, 129.98, 131.71, 136.87, 138.24, 142.19, 156.60;

HRMS (ESI⁺): m/z 400.2379 [M+H]⁺ (calcd. [C₂₆H₂₉N₃O+H]⁺ 400.2383).

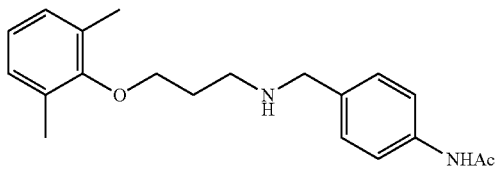

Compound 542

N-(4-((3-(2,6-Dimethylphenoxy)propylamino)methyl)phenyl)acetamide (542). Method B applied to 3-(2,6-dimethylphenoxy)propylamine and 4-acetamidobenzaldehyde, followed by purification Protocol B (MeOH/Et$_2$O) afforded the title compound (82.2 mg, 45%).
$^1$H NMR (500 MHz, CD$_3$OD) δ 2.14 (3H, NHAc), 2.18-2.24 (8H, m, 2×CH$_3$,CH$_2$CH$_2$N)8H, mB), 3.35 (2H, t, J 7.9 Hz, CH$_2$N), 3.87 (2H, t, J 5.8 Hz, CH$_2$O), 4.24 (2H, s, ArCH$_2$N), 6.90 (1H, t, J 7.5 Hz, Ar), 7.00 (2H, d, J 7.5 Hz, Ar), 7.47 (2H, d, J 8.5 Hz, Ar), 7.68 (2H, d, J 8.5, Hz Ar);
$^{13}$C NMR (100 MHz, CD$_3$OD) δ 16.42, 16.43, 23.89, 23.91, 28.13, 46.31, 51.98, 69.97, 121.41, 125.27, 127.62, 129.97, 131.69, 131.73, 141.35, 156.62, 171.85;
HRMS (ESI$^+$): m/z 327.2068 [M+H]$^+$ (calcd. [C$_{20}$H$_{26}$N$_2$O$_2$+H]$^+$ 327.2067).

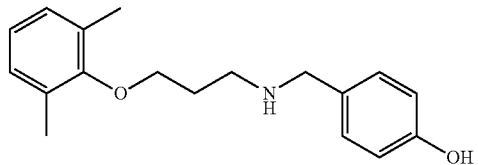

Compound 550

4-((3-(2,6-Dimethylphenoxy)propylamino)methyl)phenol (550). Method A1 applied to 3-(2,6-dimethylphenoxy)propylamine and 4-hydroxybenzaldehyde, followed by purification Protocol B (MeOH/H$_2$O) afforded the title compound (156 mg, 42%).
$^1$H NMR (500 MHz, CD$_3$OD) δ 2.19-2.25 (8H, m, 2×CH$_3$, CH$_2$CH$_2$N), 3.33-3.36 (2H, obscured m, CH$_2$N), 3.88 (2H, t, J 5.9 Hz, CH$_2$O), 4.19 (2H, s, ArCH$_2$N), 6.87-6.93 (3H, m, Ar), 7.01 (2H, d, J 7.4 Hz, Ar), 7.36-7.38 (2H, m, Ar);
$^{13}$C NMR (125 MHz, CD$_3$OD) δ 16.41, 28.12, 46.06, 52.11, 70.03, 116.95, 122.89, 125.26, 129.96, 131.69, 132.63, 156.63, 160.03;
HRMS (ESI$^+$): m/z 286.1804 [M+H]$^+$ (calcd. [C$_{18}$H$_{23}$NO$_2$+H]$^+$ 286.1807).

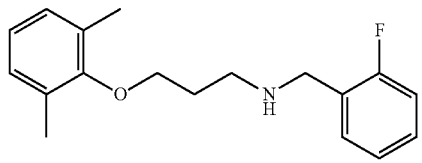

Compound 551

3-(2,6-Dimethylphenoxy)-N-(2-fluorobenzyl)propan-1-amine (551). Method A1 applied to 3-(2,6-dimethylphenoxy)propylamine and 2-fluorobenzaldehyde, followed by purification Protocol B (MeOH/H$_2$O) afforded the title compound (161 mg, 41%).
$^1$H NMR (500 MHz, CD$_3$OD) δ 2.22-2.28 (8H, m, 2×CH$_3$, CH$_2$CH$_2$N), 3.38-3.41 (2H, m, CH$_2$N), 3.88 (2H, t, J 5.9 Hz, CH$_2$O), 4.39 (2H, s, ArCH$_2$N), 6.90 (1H, t, J 7.5 Hz, Ar), 6.99 (2H, dd, J 7.4, 0.5 Hz, Ar), 7.26 (1H, ddd, J 10.0, 8.6, 1.1 Hz, Ar), 7.31 (1H, td, J 7.6, 1.0 Hz, Ar), 7.50-7.55 (1H, m, Ar), 7.64 (1H, td, J 7.6, 1.7 Hz, Ar);
$^{13}$C NMR (125 MHz, CD$_3$OD) δ 16.41, 28.02, 45.65, 45.68, 46.68, 69.97, 116.86, 117.03, 119.60, 119.72, 125.25, 126.22, 126.25, 129.96, 131.69, 133.33, 133.40, 133.49, 133.51, 156.60, 161.75, 163.72;
HRMS (ESI$^+$): m/z 288.1762 [M+H]$^+$ (calcd. [C$_{18}$H$_{22}$FNO+H]$^+$ 288.1763).

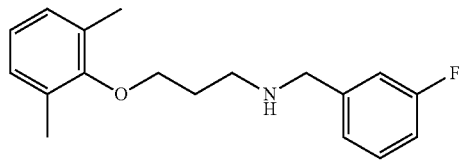

Compound 552

3-(2,6-Dimethylphenoxy)-N-(3-fluorobenzyl)propan-1-amine (552). Method A1 applied to 3-(2,6-dimethylphenoxy)propylamine and 3-fluorobenzaldehyde, followed by purification Protocol B (MeOH/H$_2$O) afforded the title compound (207 mg, 64%).
$^1$H NMR (500 MHz, CD$_3$OD) δ 2.22-2.26 (8H, m, 2×CH$_3$, CH$_2$CH$_2$N), 3.36-3.39 (2H, m, CH$_2$N), 3.88 (2H, t, J 5.9 Hz, CH$_2$O), 4.32 (2H, s, ArCH$_2$N), 6.90 (1H, dd, J 7.9, 7.1 Hz, Ar), 7.00 (2H, dd, J 7.5, 0.5 Hz, Ar), 7.22 (1H, tdd, J 8.6, 2.6, 0.7 Hz, Ar), 7.34-7.39 (2H, m, Ar), 7.51 (1H, td, J 8.0, 5.8 Hz, Ar);
$^{13}$C NMR (125 MHz, CD$_3$OD) δ 16.41, 28.14, 46.62, 51.70, 51.71, 69.93, 117.48, 117.65, 117.81, 117.99, 125.27, 126.99, 127.01, 129.97, 131.69, 132.25, 132.32, 134.97, 135.03, 156.63, 163.36, 165.32;
HRMS (ESI$^+$): m/z 288.1758 [M+H]$^+$ (calcd. [C$_{18}$H$_{22}$FNO+H]$^+$ 288.1763).

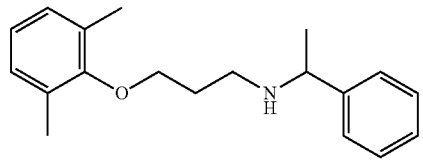

Compound 553

3-(2,6-Dimethylphenoxy)-N-(1-phenylethyl)propan-1-amine (553). Method A1 applied to 3-(2,6-dimethylphenoxy)propylamine and acetophenone, followed by purification Protocol B (MeOH/Et$_2$O) afforded the title compound (93 mg, 47%).
$^1$H NMR (500 MHz, CD$_3$OD) δ 1.71 (3H, d, J 6.8 Hz, CHCH$_3$), 2.05-2.20 (8H, m, 2×CH$_3$,CH$_2$CH$_2$N), 3.03-3.09, 3.20-3.26 (2H, 2×m, CH$_2$N), 4.45 (2H, app td, 5.2, 1.5 Hz, CH$_2$O), 6.87 (1H, m, Ar), 6.96 (2H, m, Ar), 7.44-7.52 (5H, m, Ar);
$^{13}$C NMR (125 MHz, CD$_3$OD) δ 15.5, 19.5, 28.2, 44.7, 59.8, 69.7, 125.2, 128.7, 129.9, 130.6, 130.8, 131.6, 137.5, 156.6;
HRMS (ESI$^+$): m/z 284.2021 [M+H]$^+$ (calcd. [C$_{18}$H$_{22}$FNO+H]$^+$ 284.2014).

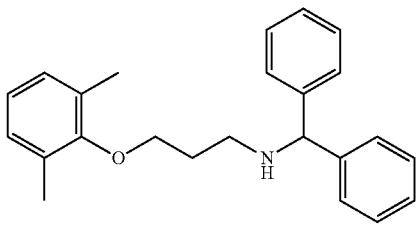

Compound 554

N-Benzhydryl-3-(2,6-dimethylphenoxy)propan-1-amine (554). Titanium tetrachloride (128.6 mg, 0.67 mmol) was added to a stirring mixture of benzophenone (112.0 mg, 0.61 mmol) and dry dichloromethane (20 mL) under $N_2$. The mixture was cooled to 0° C. and a solution of 3-(2,6-dimethylphenoxy)propan-1-amine (221.0 mg, 1.23 mmol) in dry dichloromethane (10 mL) was added. After stirring at r.t. for 3 h a solution of NaCNBH$_3$ in methanol (45 mg, 0.70 mmol, 20 mL) was added and stifling continued for 1 h. 20% Aq. NaOH (1.0 mL) was added, the mixture was filtered and the filtrate partitioned between EtOAc and 0.3 M NaOH. The organic layer was separated and concentrated under reduced pressure. Purification according to Protocol B gave the product (MeOH/H$_2$O) afforded the title compound (92.0 mg, 43%).

$^1$H NMR (500 MHz, CD$_3$OD) δ 2.15 (6H, s, 2×CH$_3$), 2.23-2.29 (2H, m, CH$_2$CH$_2$N), 3.28-3.30 (2H, m, CH$_2$N), 3.81 (2H, t, J 5.8 Hz, CH$_2$N), 5.65 (1H, s, CH(Ph)$_2$), 6.87 (1H, dd, J 8.0, 7.0 Hz, Ar), 6.95-6.97 (2H, m, Ar), 7.41-7.45 (2H, m, Ar), 7.47-7.51 (4H, m, Ar), 7.57-7.60 (4H, m, Ar);

$^{13}$C NMR (125 MHz, CD$_3$OD) δ 16.39, 28.06, 45.98, 67.28, 69.68, 125.22, 128.81, 129.95, 130.45, 130.57, 131.61, 137.01, 156.57;

HRMS (ESI$^+$): m/z 346.2163 [M+H]$^+$ (calcd. [C$_{24}$H$_{27}$NO+ H]$^+$ 346.2165).

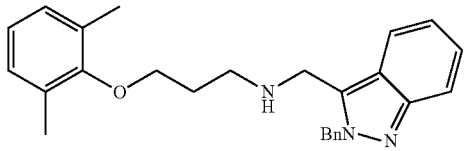

Compound 555

2-Benzyl-2H-indazole-3-carbaldehyde (intermediate-28). Benzyl bromide (290 μL, 2.45 mmol) was added to a stirring mixture of 1H-3-formylindazole (299 mg, 2.04 mmol) in dry DMF (10 mL). The mixture was heated at 120° C. under N$_2$ for 6 h, with additional benzyl bromide (145 μL, 1.22 mmol) added after 3 h. The mixture was cooled to r.t., poured into H$_2$O (20 mL) and extracted with dichloromethane (3×10 mL). The combined organic extracts were washed with sat. aq. NaCl (10 mL), dried (MgSO$_4$), filtered and concentrated under reduced pressure. Flash chromatography (1% Et$_2$O/ petroleum spirits) gave a mixture of N1 and N2-benzylated products. Pure 2-benzyl-2H-indazole-3-carbaldehyde (126 mg, 26%) was obtained by crystallizing from methanol/ H$_2$O, m.p. 90-91° C.;

$^1$H NMR (500 MHz, CDCl$_3$) δ 6.04 (2H, s, PhCH$_2$), 7.26-7.43 (6H, m, Ar), 7.88 (1H, d, J 8.4 Hz, Ar), 8.01 (1H, d, J 8.0 Hz, Ar), 10.29 (1H, s, CHO);

$^{13}$C NMR (125 MHz, CDCl$_3$) δ 56.88, 118.53, 119.10, 125.65, 126.56, 126.94, 127.98, 128.48, 128.92, 129.99, 135.89, 147.96, 177.38;

HRMS (ESI$^+$): m/z 237.1020 [M+H]$^+$ (calcd. [C$_{15}$H$_{12}$N$_2$O+ H]$^+$ 237.1022).

N-((2-Benzyl-2H-indazol-3-yl)methyl)-3-(2,6-dimethylphenoxy)propan-1-amine (555). Method A1 applied to 3-(2, 6-dimethylphenoxy)propylamine and intermediate-28, followed by purification Protocol B (MeOH/Et$_2$O) afforded the title compound (10.3 mg, 33%).

$^1$H NMR (500 MHz, CD$_3$OD) δ 2.16-2.24 (8H, m, 2×CH$_3$, CH$_2$CH$_2$N), 3.42 (2H, t, J 7.9 Hz, CH$_2$N), 3.84 (2H, t, J 5.8 Hz, CH$_2$O), 4.82 (2H, s, ArCH$_2$NCH$_2$), 5.89 (2H, s, PhCH$_2$), 6.90 (1H, dd, J 8.0, 6.9 Hz, Ar), 6.99 (2H, d, J 7.5 Hz, Ar), 7.15 (2H, dd, J 7.8, 1.0 Hz, Ar), 7.25 (1H, ddd, J 8.5, 6.7, 0.8 Hz, Ar), 7.29-7.35 (3H, m, Ar), 7.40 (1H, ddd, J 8.8, 6.7, 1.0 Hz, Ar), 7.70 (1H, dt, J 8.8, 0.9 Hz, Ar), 7.91 (1H, dt, J 8.5, 1.0 Hz, Ar);

$^{13}$C NMR (100 MHz, CD$_3$OD) δ 16.4, 28.4, 41.0, 47.2, 55.7, 70.00, 118.4, 120.3, 124.1, 124.5, 125.3, 127.9, 128.2, 129.4, 130.0, 130.1, 131.7, 137.4, 149.4, 156.5;

HRMS (ESI$^+$): m/z 400.2389 [M+H]$^+$ (calcd. [C$_{26}$H$_{29}$N$_3$O+ H]$^+$ 400.2383).

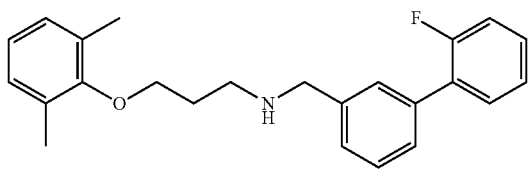

Compound 556

3-(2,6-Dimethylphenoxy)-N-((2'-fluorobiphenyl-3-yl) methyl)propan-1-amine (556). Pd(dppt)Cl$_2$ was added to a degassed (N$_2$) mixture of 2-fluorophenylboronic acid (190.0 mg, 1.36 mmol), N-(3-bromobenzyl)-3-(2,6-dimethylphenoxy)propan-1-amine (349 mg, 0.907 mmol), Cs$_2$CO$_3$ (884 mg, 2.70 mmol) and dry dioxane. The mixture was heated at 120° C. with stirring until the bromide was consumed. The mixture was diluted with EtOAc (10 mL) and extracted with sat. aq. NaHCO$_3$ (10 mL). Purification by Protocol B (MeOH/Et$_2$O) afforded the title compound (295 mg, 84%).

$^1$H NMR (500 MHz, CD$_3$OD) δ 2.20-2.26 (8H, m, 2×CH$_3$, CH$_2$CH$_2$N), 3.38-3.41 (2H, m, CH$_2$N), 3.88 (2H, t, J 5.8 Hz, CH$_2$O), 4.36 (2H, s, ArCH$_2$N), 6.90 (1H, dd, J 8.0, 7.0 Hz, Ar), 6.99 (2H, dd, J 7.5, 0.5 Hz, Ar), 7.21 (1H, ddd, J 11.0, 8.3, 1.1 Hz, Ar), 7.27 (1H, td, J 7.5, 1.2 Hz, Ar), 7.41 (1H, dddd, J 8.2, 7.4, 5.1, 1.8 Hz, Ar), 7.51 (1H, td, J 7.8, 1.8 Hz, Ar), 7.55-7.60 (2H, m, Ar), 7.66 (1H, dq, J 7.4, 1.6 Hz, Ar), 7.74 (1H, d, J 1.4 Hz, Ar);

$^{13}$C NMR (125 MHz, CD$_3$OD) δ 16.39, 28.13, 46.52, 52.32, 69.98, 117.01, 117.19, 125.30, 125.84, 125.87, 129.27, 129.38, 129.99, 130.26, 130.55, 130.90, 130.96, 131.38, 131.40, 131.64, 131.66, 131.69, 131.85, 131.88, 132.87, 138.34, 156.60, 160.08, 162.04;

HRMS (ESI$^+$): m/z 364.2069 [M+H]$^+$ (calcd. [C$_{24}$H$_{26}$FNO+ H]$^+$ 364.2071).

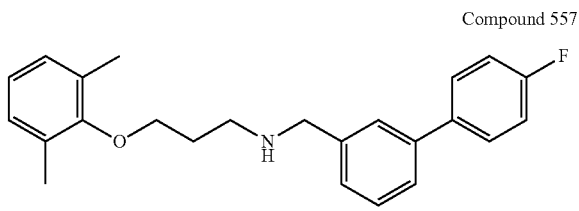

Compound 557

3-(2,6-Dimethylphenoxy)-N-((4'-fluorobiphenyl-3-yl)methyl)propan-1-amine (557). Prepared from 4-fluorophenylboronic acid and N-(3-bromobenzyl)-3-(2,6-dimethylphenoxy)propan-1-amine as per compound 556, followed by purification by Protocol B (MeOH/Et$_2$O) afforded the title compound (196 mg, 45%).
$^1$H NMR (500 MHz, CD$_3$OD) δ 2.23-2.27 (8H, m, 2×CH$_3$, CH$_2$CH$_2$N), 3.39-3.42 (2H, m, CH$_2$N), 3.89 (2H, t, J 5.8 Hz, CH$_2$O), 4.37 (2H, s, ArCH$_2$N), 6.90 (1H, dd, J 8.0, 6.9 Hz, Ar), 6.99 (2H, dd, J 7.5, 0.6 Hz, Ar), 7.16-7.20 (2H, m, Ar), 7.51-7.53 (1H, m, Ar), 7.56 (1H, td, J 7.6, 0.3 Hz, Ar), 7.66-7.72 (3H, m, Ar), 7.81 (1H, t, J 1.6 Hz, Ar);
$^{13}$C NMR (125 MHz, CD$_3$OD) δ 16.41, 28.10, 46.47, 52.32, 69.98, 116.63, 116.80, 125.31, 129.19, 129.66, 129.85, 129.92, 129.99, 130.94, 131.70, 133.16, 137.71, 137.74, 142.53, 156.59, 163.21, 165.16;
HRMS (ESI$^+$): m/z 364.2071 [M+H]$^+$ (calcd. [C$_{24}$H$_{26}$FNO+H]$^+$ 364.2071).

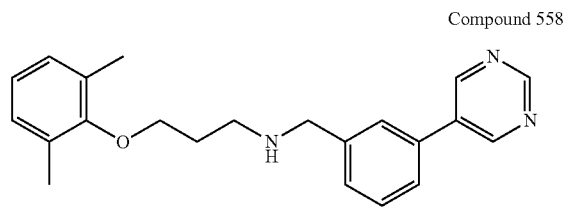

Compound 558

3-(2,6-Dimethylphenoxy)-N-(3-(pyrimidin-5-yl)benzyl)propan-1-amine (558). Prepared from pyrimidin-5-ylboronic acid and N-(3-bromobenzyl)-3-(2,6-dimethylphenoxy)propan-1-amine as per compound 556. Purification by Protocol B (MeOH/H$_2$O) afforded the title compound (60 mg, 21%). $^1$H NMR (500 MHz, CD$_3$OD) δ 2.23-2.27 (8H, m, 2×CH$_3$,CH$_2$CH$_2$N), 3.41-3.44 (2H, m, CH$_2$N), 3.89 (2H, t, J 5.8 Hz, CH$_2$O), 4.41 (2H, s, ArCH$_2$N), 6.90 (1H, dd, J 7.9, 7.0 Hz, Ar), 6.99 (2H, d, J 7.5 Hz, Ar), 7.67-7.70 (2H, m, Ar), 7.84-7.88 (1H, m, Ar), 7.94 (1H, s, Ar), 9.12 (2H, s, Ar), 9.17 (1H, s, Ar); $^{13}$C NMR (125 MHz, CD$_3$OD) δ 16.41, 28.15, 46.58, 52.10, 69.93, 125.31, 129.40, 129.89, 129.99, 131.53, 131.66, 131.73, 133.89, 135.17, 136.36, 156.19, 156.58, 158.37; HRMS (ESI$^+$): m/z 348.2066 [M+H]$^+$ (calcd. [C$_{22}$H$_{25}$N$_3$O+H]$^+$ 348.2075).

Compound 559

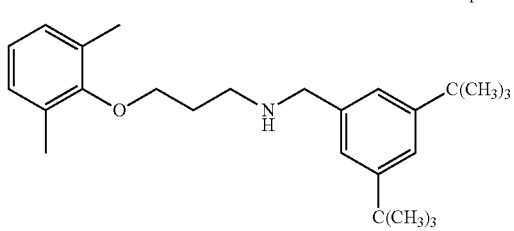

N-(3,5-Di-tert-butylbenzyl)-3-(2,6-dimethylphenoxy)propan-1-amine (559). A mixture of 3-(2,6-dimethylphenoxy)propan-1-amine (316 mg, 1.76 mmol), 3,5-di-t-butylbenzyl bromide (250 mg, 0.88 mmol) and dry THF (25 mL) was heated at reflux for 24 h. The mixture was concentrated under reduced pressure, 10% aq. NaOH (50 mL) was added and the mixture extracted with EtOAc (2×50 mL). The combined organic extracts were washed with sat. aq. NaCl, dried (MgSO$_4$), filtered and concentrated under reduced pressure. Purification by Protocol B (MeOH/H$_2$O) afforded the title compound (146 mg, 20%). $^1$H NMR (500 MHz, CD$_3$OD) δ 1.34 (18H, s, 2×C(CH$_3$)$_3$), 2.20-2.25 (8H, m, 2×CH$_3$,CH$_2$CH$_2$N), 3.35-3.39 (2H, m, CH$_2$N), 3.88 (2H, t, J 5.8 Hz, CH$_2$O), 4.27 (2H, s, ArCH$_2$N), 6.90 (1H, t, J 7.5 Hz, Ar), 7.00 (2H, dd, J 7.4, 0.5 Hz, Ar), 7.39 (2H, d, J 1.8 Hz, Ar), 7.55 (1H, t, J 1.8 Hz, Ar); $^{13}$C NMR (125 MHz, CD$_3$OD) δ 16.43, 28.06, 31.77, 35.85, 46.46, 52.96, 70.05, 124.80, 125.25, 125.33, 130.00, 131.66, 131.75, 153.32, 156.57; HRMS (ESI$^+$): m/z 382.3107 [M+H]$^+$ (calcd. [C$_{26}$H$_{39}$NO+H]$^+$ 382.3109).

Compound 562

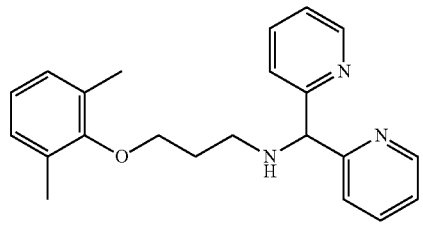

3-(2,6-Dimethylphenoxy)-N-(dipyridin-2-ylmethyl)propan-1-amine (562). Method A2 applied to carbonyl di(2-pyridine) and 3-(2,6-dimethylphenoxy)propylamine, followed by purification Protocol B (EtOH/H$_2$O) afforded the title compound (643 mg, 24%). $^1$H NMR (500 MHz, CD$_3$OD) δ 2.21 (6H, s, 2×CH$_3$), 2.31-2.36 (2H, m, CH$_2$CH$_2$N), 3.41 (2H, t, J 7.7 Hz, CH$_2$N), 3.88 (2H, t, J 5.8, CH$_2$O), 6.26 (1H, s, CH(Ar)$_2$), 6.88 (1H, t, J 7.5 Hz, Ar), 6.97 (2H, d, J 7.5 Hz, Ar), 7.69 (2H, ddd, J 7.7, 5.2, 1.0 Hz, Ar), 7.91 (2H, d, J 7.9 Hz, Ar), 8.17 (2H, td, J 7.8, 1.7 Hz, Ar), 8.81 (2H, dt, J 5.1, 0.8 Hz, Ar); $^{13}$C NMR (125 MHz, CD$_3$OD) δ 16.49, 28.15, 46.45, 64.14, 70.11, 125.24, 126.22, 127.02, 129.94, 131.65, 142.33, 149.33, 151.95, 156.62; HRMS (ESI$^+$): m/z 348.2077 [M+H]$^+$ (calcd. [C$_{22}$H$_{25}$N$_3$O+H]$^+$ 348.2075).

Compound 642

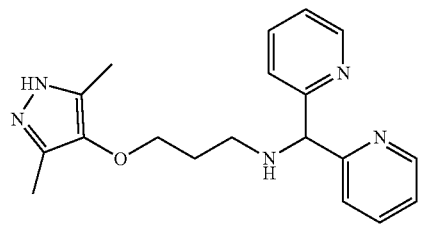

N-(3-(3,5-Dimethyl-1H-pyrazol-4-yloxy)propyl)phthalimide (intermediate-20). A mixture of 3,5-dimethyl-1H-pyrazol-4-ol (386 mg, 3.44 mmol), N-(3-bromopropyl)phthalimide (1.16 g, 3.78 mmol), Cs$_2$CO$_3$ (2.24 g, 6.88 mmol) and acetone (20 mL) was heated at reflux for 16 h.

The mixture was filtered and concentrated under reduced pressure to give a thick oil, which was purified by flash chromatography (90% EtOAc/petroleum spirits) gave the title compound (290 mg, 25%).

$^1$H NMR (400 MHz, CDCl$_3$) δ 2.07 (2H, dd, J 13.6, 6.4 Hz, CH$_2$CH$_2$N), 2.19 (6H, s, 2×CH$_3$), 3.86 (4H, td, J 6.6, 4.7 Hz, CH$_2$N,CH$_2$O), 7.67 (2H, dd, J 5.4, 3.1, AR), 7.81 (2H, dd, J5.5, 3.1 HZ, Ar);

$^{13}$C NMR (100 MHz, CDCl$_3$) δ 9.85, 29.24, 35.43, 72.04, 123.25, 132.13, 133.99, 134.61, 138.93, 168.39;

HRMS (ESI$^+$): m/z 300.1341 [M+H]$^+$ (calcd. [C$_{16}$H$_{17}$N$_3$O$_3$+H]$^+$ 300.1343).

3-(3,5-Dimethyl-1H-pyrazol-4-yloxy)propan-1-amine (intermediate-21). A mixture of the phthalimide intermediate-20 (192.3 mg, 0.644 mmol), hydrazine hydrate (193.4 mg, 3.86 mmol) and ethanol (11 mL) was heated in an oil bath at 100° C. for 16 h under N$_2$. After cooling to 0° C. the mixture was filtered and the filtrate was concentrated under reduced pressure. The residue was washed triturated with 14:5:1 CH$_2$Cl$_2$/MeOH/H$_2$O, the liquid fraction was concentrated to give enriched (~90% pure by $^1$H NMR) amine, which was used in subsequent reactions without further purification (94.8 mg, 87%).

$^1$H NMR (500 MHz, CD$_3$OD) δ 1.85 (2H, quint, J 7.0 Hz, CH$_2$CH$_2$N), 2.15 (6H, s, 2×CH$_3$), 2.85 (2H, t, J 7.0 Hz, CH$_2$N), 3.88 (2H, t, CH$_2$O);

$^{13}$C NMR (125 MHz, CD$_3$OD) δ 9.65, 33.92, 39.82, 73.87, 135.62 (2 C, br s), 140.1;

HRMS (ESI$^+$): m/z 170.1301 [M+H]$^+$ (calcd. [C$_8$H$_{15}$N$_3$O+H]$^+$ 170.1288).

3-(3,5-Dimethyl-1H-pyrazol-4-yloxy)-N-(dipyridin-2-ylmethyl)propan-1-amine (642). Method A2 applied to carbonyl di(2-pyridine) and intermediate-21, followed by purification Protocol B (THF/EtOH) afforded the title compound (70.0 mg, 64%). $^1$H NMR (600 MHz, CD$_3$OD) δ 2.26-2.30 (2H, m, CH$_2$CH$_2$N), 2.36 (6H, s, 2×CH$_3$), 3.28-3.30 (2H, m, CH$_2$N), 4.11 (2H, t, J 5.9 Hz, CH$_2$O), 5.98 (1H, s, CH(Ar)$_2$), 7.46-7.48 (2H, m, Ar), 7.62 (2H, d, J 7.9 Hz, Ar), 7.92-7.95 (2H, m, Ar), 8.68 (2H, dd, J 4.9, 0.7 Hz, Ar); $^{13}$C NMR (150 MHz, CD$_3$OD) δ 8.58, 8.58, 27.78, 27.78, 45.45, 45.45, 66.22, 66.22, 73.42, 73.42, 124.83, 124.83, 124.92, 124.92, 125.78, 125.78, 137.88, 137.88, 139.68, 139.68, 139.88, 139.88, 140.43, 140.43, 150.60, 150.60, 150.72, 150.72, 154.28, 154.28; HRMS (ESI$^+$): m/z 338.1975 [M+H]$^+$ (calcd. [C$_{19}$H$_{23}$N$_5$O+H]$^+$ 338.1975).

Compound 643

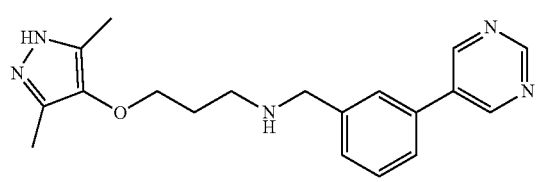

3-(3,5-Dimethyl-1H-pyrazol-4-yloxy)-N-(3-(pyrimidin-5-yl)benzyl)propan-1-amine (643)

Method A1 applied to 3-(pyrimidin-5-yl)benzaldehyde and intermediate-21, followed by purification Protocol B (THF/EtOH) afforded the title compound (63.0 mg, 31%).

$^1$H NMR (600 MHz, CD$_3$OD) δ 2.23-2.28 (2H, m, CH$_2$CH$_2$N), 2.37 (6H, s, 2×CH$_3$), 3.37 (2H, t, J 7.8, CH$_2$N), 4.12 (2H, t, J 6.0 Hz, CH$_2$O), 4.41 (2H, s, ArCH$_2$N), 7.66 (1H, t, J 7.7 Hz, Ar), 7.71 (1H, d, J 7.6 Hz, Ar), 7.85 (1H, d, J 7.7 Hz, Ar), 8.04 (1H, s, Ar), 9.18 (3H, d, J 5.4 Hz, Ar);

$^{13}$C NMR (150 MHz, CD$_3$OD) δ 8.73, 27.8, 46.0, 52.2, 73.1, 129.19, 129.34, 129.95, 130.15, 131.42, 131.85, 131.91, 133.92, 135.24, 136.09, 137.78, 140.41, 156.22, 158.12;

HRMS (ESI$^+$): m/z 338.1978 [M+H]$^+$ (calcd. [C$_{19}$H$_{23}$N$_5$O+H]$^+$ 338.1975).

Compound 644

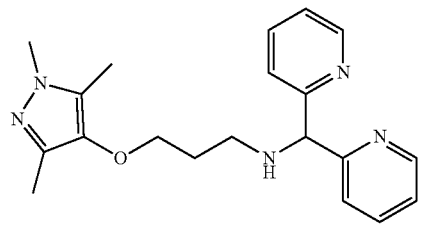

N-(Dipyridin-2-ylmethyl)-3-(1,3,5-trimethyl-1H-pyrazol-4-yloxy)propan-1-amine (644)

Method A2 applied to carbonyl di(2-pyridine) and intermediate-21, followed by purification Protocol B (EtOH/Et$_2$O) afforded the title compound (225 mg, 27%).

$^1$H NMR (400 MHz, CD$_3$OD) δ 2.25-2.35 (8H, m, 2×CH$_3$, CH$_2$CH$_2$N), 3.28-3.31 (2H, m, CH$_2$N), 3.90 (3H, s, NCH$_3$), 4.09 (2H, t, J 5.9 Hz, CH$_2$O), 5.99 (1H, s, CH(Ar)$_2$), 7.46 (2H, ddd, J 7.6, 4.9, 1.1 Hz, Ar), 7.63 (2H, dd, J 7.9, 0.9, Ar), 7.92 (2H, td, J 7.8, 1.8, Ar);

$^{13}$C NMR (125 MHz, CD$_3$OD) δ 8.3, 8.9, 27.7, 36.0, 45.5, 66.4, 73.8, 111.4, 124.7, 125.6, 137.1, 138.3, 139.4, 140.3, 150.8, 154.6;

HRMS (ESI$^+$): m/z 352.2134 [M+H]$^+$ (calcd. [C$_{20}$H$_{25}$N$_5$O+H]$^+$ 352.2132).

Compound 645

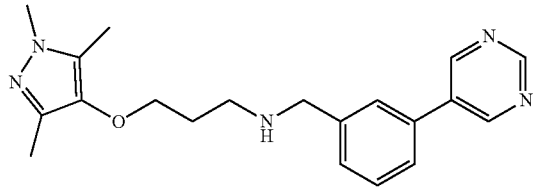

4-(3-Bromopropoxy)-1,3,5-trimethyl-1H-pyrazole (intermediate-22). A mixture of 1,3,5-trimethyl-1H-pyrazole (320 mg, 2.91 mmol), N-(3-bromopropyl)phthalimide (587 mg, 2.91 mmol), K$_2$CO$_3$ (2.01 g, 14.3 mmol) and DMF (30 mL) was heated at 60° C. for 4 h. The mixture was cooled to r.t., filtered, concentrated under reduced pressure and partitioned between EtOAc and sat. aq. NaHCO$_3$ (20 mL of each). The organic layer was separated and the aqueous layer extracted with EtOAc (2×10 mL). The combined organic extracts were sequentially washed with sat. aq. NaHCO$_3$ (20 mL), H$_2$O (20 mL), then sat. aq. NaCl (20 mL), dried (MgSO$_4$), filtered and concentrated under reduced pressure. The residue was purified by flash chromatography (4:4:1→3:5:1 toluene/CH$_2$Cl$_2$/acetone) to give the title compound (225.6 mg, 31%).

¹H NMR (500 MHz, CDCl₃) δ 2.08 (3H, s, CH₃), 2.10 (3H, s, CH₃), 2.13 (2H, CH₂CH₂N), 3.55 (2H, t, J 6.0 Hz, CH₂Br), 3.57 (3H, s, NCH₃), 3.83 (2H, t, J 6.0 Hz, CH₂O);
¹³C NMR (125 MHz, CDCl₃) δ 8.42, 10.69, 30.03, 32.86, 36.19, 128.87, 138.24, 138.74;
HRMS (ESI⁺): m/z 247.0441 [M+H]⁺ (calcd. [C₉H₁₅BrN₂O+H]⁺ 247.0441).

4-(3-Azidopropoxy)-1,3,5-trimethyl-1H-pyrazole (intermediate-23). A mixture of intermediate-22 (482 mg, 1.95 mmol), NaN₃ (140 mg, 2.15 mmol) and DMSO (5 mL) was heated at 60° C. for 5 h, then 100° C. for 2 h. Water (20 mL) was added and the mixture was extracted with Et₂O (2×50 mL). The combined organic extracts were washed with H₂O (50 mL), dried (MgSO₄). Flash chromatography (4:1 toluene/acetone) gave the title compound (168 mg, 94%).
¹H NMR (400 MHz, CDCl₃) δ 1.83-1.89 (2H, m, CH₂CH₂O), 2.06 (3H, s, CH₃), 2.08 (3H, s, CH₃), 3.44 (2H, t, J 6.7 Hz, CH₂N), 3.55 (3H, s, CH₃), 3.76 (2H, t, J 6.0 Hz, CH₂O);
¹³C NMR (100 MHz, CDCl₃) δ 8.34, 10.64, 29.28, 36.13, 48.06, 71.09, 128.73, 138.09, 138.79;
HRMS (ESI⁺): m/z 210.1344 [M+H]⁺ (calcd. [C₉H₁₇N₃O+H]⁺ 210.1349).

N-(3-(Pyrimidin-5-yl)benzyl)-3-(1,3,5-trimethyl-1H-pyrazol-4-yloxy)propan-1-amine (645)

Method A1 (except amine:aldehyde ratio reversed to be 1.2:1) applied to 3-(pyrimidin-5-yl)benzaldehyde and intermediate-23, followed by purification Protocol B (EtOH/THF/Et₂O) afforded the title compound (38.3 mg, 36%).
¹H NMR (600 MHz, CD₃OD) δ 2.09 (3H, s, CH₃), 2.14-2.19 (5H, m, CH₃,CH₂CH₂N), 3.34 (2H, t, J 7.9 Hz,CH₂N), 3.62 (3H, s, CH₃), 3.92 (2H, t, J 5.9 Hz, CH₂O), 4.39 (2H, s, ArCH₂N), 7.66-7.69 (2H, m, Ar), 7.84-7.87 (1H, m, Ar), 7.94 (1H, s, Ar), 9.11 (2H, s, Ar), 9.17 (1H, s, Ar);
¹³C NMR (125 MHz, CD₃OD) δ 8.45, 10.60, 28.02, 36.25, 46.38, 52.14, 72.96, 111.39, 129.16, 129.82, 131.18, 131.43, 131.72, 134.31, 135.16, 136.16, 139.21, 139.92, 156.17, 158.26;
HRMS (ESI⁺): m/z 352.2139 [M+H]⁺ (calcd. [C₂₀H₂₅N₅O+H]⁺ 352.2132).

Example 2

In Vitro Structure-Activity Screening of Compounds in the Sodium Channel, Site 2 of Rat Forebrain Membranes (Demonstrating Binding in the Inactivated State)

Rat forebrains were homogenized in 20 volumes of Tris buffer (50 mM, pH 7.4) and centrifuged at 30,000 g for 10 min. The supernatant was discarded and the pellet resuspended in fresh Tris buffer and the homogenization and centrifugation procedure repeated twice to give a preparation of washed rat brain membranes. Aliquots of washed rat brain membranes were incubated with [³H]batrachotoxinin (5 nM) in the absence or presence of increasing concentrations of compounds, added as solutions in dimethyl sulfoxide. After incubation at 37° C. for 60 min, membranes were collected by rapid filtration through glass fibre filters under vacuum and radioactivity in the filters was determined by liquid scintillation counting. Non-specific binding of [³H] batrachotoxinin to brain membranes was determined by incubating membranes in the presence of veratridine (100 µM). Data was plotted with specific binding against log₁₀ compound concentrations and the concentration of each compound that inhibited specific binding of ³H-batrachotoxinin by 50% (IC₅₀) was computed using a standard non-linear regression equation.

The results are depicted in Table 2.1

TABLE 2.1

IC₅₀ values for compounds binding to sodium channel site 2 in rat membranes in competition with [³H]batrachotoxinin

| Compound | IC₅₀ (µM) | Structure |
|---|---|---|
| 504 | >0.9 | 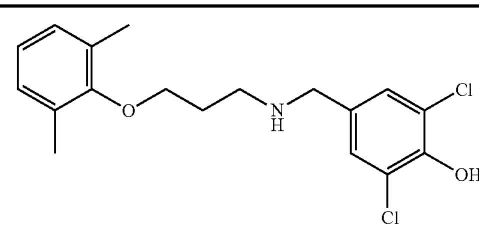 |
| 518 | 0.404 | 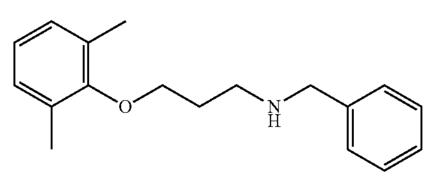 |
| 519 | 0.68 | 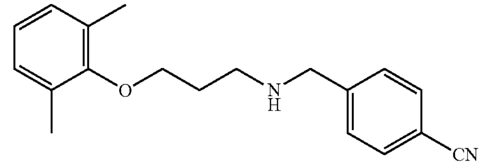 |

TABLE 2.1-continued

IC$_{50}$ values for compounds binding to sodium channel site 2 in rat
membranes in competition with [$^3$H]batrachotoxinin

| Compound | IC$_{50}$ (μM) | Structure |
|---|---|---|
| 520 | 0.438 | 2,6-dimethylphenyl-O-(CH$_2$)$_3$-NH-CH$_2$-(4-OMe-phenyl) |
| 521 | 0.57 | 2,6-dimethylphenyl-O-(CH$_2$)$_3$-NH-CH$_2$-(4-F-phenyl) |
| 522 | <0.3 | 2,6-dimethylphenyl-O-(CH$_2$)$_3$-NH-CH$_2$-(4-Ph-phenyl) |
| 523 | 2.06 | 2,6-dimethylphenyl-O-(CH$_2$)$_3$-NH-CH$_2$-(2-pyridyl) |
| 524 | 0.535 | 2,6-dimethylphenyl-O-(CH$_2$)$_3$-NH-CH$_2$-(3-CF$_3$-phenyl) |
| 525 | 0.34 | 2,6-dimethylphenyl-O-(CH$_2$)$_3$-NH-CH$_2$-(3-OMe-phenyl) |
| 526 | 0.375 | 2,6-dimethylphenyl-O-(CH$_2$)$_3$-NH-CH$_2$-(4-CF$_3$-phenyl) |
| 528 | >0.9 | 2,6-dimethylphenyl-O-(CH$_2$)$_3$-NH-CH$_2$-(3-pyridyl) |

TABLE 2.1-continued

IC$_{50}$ values for compounds binding to sodium channel site 2 in rat
membranes in competition with [$^3$H]batrachotoxinin

| Compound | IC$_{50}$ (μM) | Structure |
| --- | --- | --- |
| 530 | >0.9 | 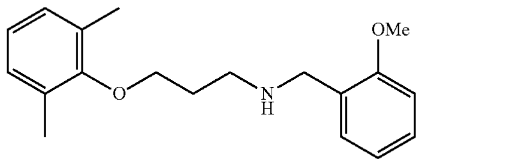 |
| 531 | 0.359 | 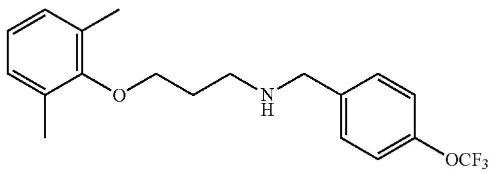 |
| 532 | >0.9 | 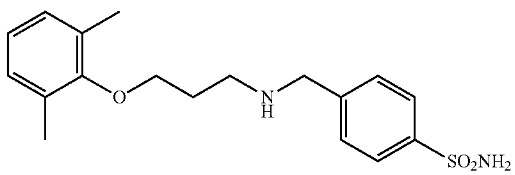 [SMILES: Cc1cccc(C)c1OCCCNCc1ccc(S(N)(=O)=O)cc1] |
| 533 | 0.468 | 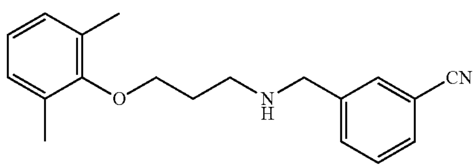 [SMILES: Cc1cccc(C)c1OCCCNCc1cccc(C#N)c1] |
| 534 | 0.444 | 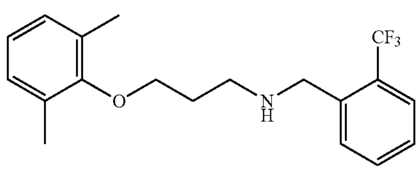 [SMILES: Cc1cccc(C)c1OCCCNCc1ccccc1C(F)(F)F] |
| 535 | 0.159 | 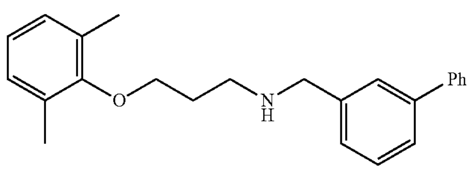 [SMILES: Cc1cccc(C)c1OCCCNCc1cccc(-c2ccccc2)c1] |
| 536 | 0.2 | 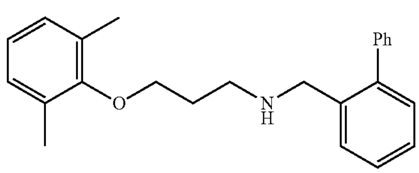 [SMILES: Cc1cccc(C)c1OCCCNCc1ccccc1-c1ccccc1] |
| 538 | >0.9 | 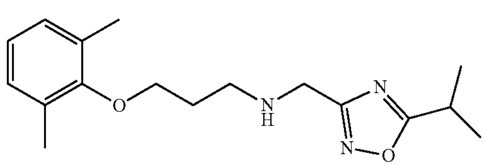 [SMILES: Cc1cccc(C)c1OCCCNCc1noc(C(C)C)n1] |
| 540 | 0.14 | 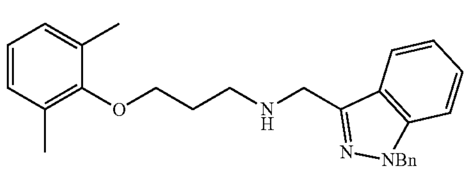 [SMILES: Cc1cccc(C)c1OCCCNCc1nn(Cc2ccccc2)c2ccccc12] |

TABLE 2.1-continued

IC$_{50}$ values for compounds binding to sodium channel site 2 in rat membranes in competition with [$^3$H]batrachotoxinin

| Compound | IC$_{50}$ (µM) | Structure |
|---|---|---|
| 542 | >0.9 | (structure with NHAc) |
| 550 | 1.19 | (structure with OH) |
| 551 | 0.793 | (structure with 2-F phenyl) |
| 552 | 0.733 | (structure with 3-F phenyl) |
| 553 | 0.53 | (structure with α-methylbenzyl) |

Example 3

Test Protocol for Determining the Potency of Compounds on Na$_v$1.2 and Na$_v$1.6 Subtypes of Voltage-Gated Sodium Ion Channels Expressed in Mammalian Cells Cell culture procedures: Chinese hamster ovary (CHO) cells were stably transfected with the cDNA sequence of either the human SCN2A or SCN8A genes to create hNa$_v$1.2 or hNa$_v$1.6 cells respectively. The cell lines were cultured in Ham's F-12 medium supplemented with 10% fetal bovine serum and antibiotics in a tissue incubator at 37° C. under a humidified air/CO$_2$ mixture (95/5 v/v). On the day of the experiment, cells were washed twice with Hank's balanced salt solution, treated with trypsin, and resuspended in fresh culture media at a density of 4–6×10$^6$ cells in 20 ml. Immediately before placing in the IonWorks Quattro instrument, cells were washed in Hank's balanced salt solution to remove culture medium and re-suspended in 3 ml of Hank's balanced salt solution.

Automated patch clamp recordings of cells using the IonWorks Quattro Instrument: The assay used a 384 microwell plate, which enabled 20 compounds to be studied at four different concentrations in quadruplicate as well as allowing a vehicle control group and a positive control group using mexiletine at 8 different concentrations. Cells were added to the wells of the Population Patch Clamp planar electrode using a 48-channel pipettor in a volume of 6 µL, per well. After 5 minutes incubation at ambient temperature with compounds or vehicle, membrane currents were recorded using the patch clamp amplifier. Block of hNa$_v$1.2 or hNa$_v$1.6 channels was measured using a stimulus voltage pattern as shown in FIG. 1. The pulse pattern was repeated twice, before and after compound addition and peak current amplitudes were measured at three test pulses, TP1, TP11 and TP12 to measure Tonic Block, 10 Hz Frequency-dependent Block and Inactivation State Block, respectively.

Data analysis: Data acquisition and analyses were carried out using the IonWorks Quattro system operation software which uses an algorithm to correct data for leak currents. Concentration-response curves were fitted by non-linear least squares regression allowing calculation of an IC$_{50}$ value (µM), being the concentration of the compound producing half-maximal inhibition.

The results are depicted in Table 3.1

TABLE 3.1

Inhibition of Na$_v$1.2 and Na$_v$1.6 channels

| Compound | Type of Block | IC$_{50}$ (μM) Na$_v$1.2 | Na$_v$1.6 |
|---|---|---|---|
| 504 | Tonic | >10 | >10 |
|  | 10 Hz | >10 | >10 |
|  | Inactivated state | 4.4 | >10 |
| 559 | Tonic | >10 | >10 |
|  | 10 Hz | >10 | >10 |
|  | Inactivated state | >10 | >10 |
| 518 | Tonic | 3.3 | 5.2 |
|  | 10 Hz | 1.8 | 2.9 |
|  | Inactivated state | 0.5 | 2.0 |
| 519 | Tonic | >10 | 5.6 |
|  | 10 Hz | 8.3 | 3.4 |
|  | Inactivated state | 2.1 | 1.8 |
| 520 | Tonic | 6.3 | 4.9 |
|  | 10 Hz | 2.1 | 2.6 |
|  | Inactivated state | 1.0 | 1.5 |
| 521 | Tonic | ≈10.2 | 4.5 |
|  | 10 Hz | 8.4 | 2.2 |
|  | Inactivated state | 2.8 | 1.4 |
| 522 | Tonic | >1000 | >1000 |
|  | 10 Hz | >1000 | >1000 |
|  | Inactivated state | >1000 | >1000 |
| 526 | Tonic | >10 | 6.9 |
|  | 10 Hz | 9.5 | 4.7 |
|  | Inactivated state | 3.5 | 2.3 |
| 531 | Tonic | 12.5 | 137.8 |
|  | 10 Hz | 3.6 | 56.3 |
|  | Inactivated state | 1.4 | 40.9 |
| 550 | Tonic | >10 | >10 |
|  | 10 Hz | 5.1 | 4.8 |
|  | Inactivated state | 2.2 | 2.2 |
| 532 | Tonic | >10 | >10 |
|  | 10 Hz | >10 | >10 |
|  | Inactivated state | 6.1 | 8.5 |
| 542 | Tonic | >10 | >10 |
|  | 10 Hz | >10 | >10 |
|  | Inactivated state | 5.0 | 7.1 |
| 524 | Tonic | >10 | 7.8 |
|  | 10 Hz | 9.6 | 3.9 |
|  | Inactivated state | >10 | >10 |
| 528 | Tonic | 34.4 | 31.7 |
|  | 10 Hz | 13.1 | 12.4 |
|  | Inactivated state | 4.8 | 4.7 |
| 525 | Tonic | 4.8 | 7.9 |
|  | 10 Hz | 1.5 | 3.2 |
|  | Inactivated state | 0.4 | 1.8 |
| 533 | Tonic | ≈10.1 | 7.1 |
|  | 10 Hz | 6.1 | 4.3 |
|  | Inactivated state | 2.0 | 2.3 |
| 535 | Tonic | 66.5 | >1000 |
|  | 10 Hz | 20.7 | >1000 |
|  | Inactivated state | 7.0 | >1000 |
| 552 | Tonic | 9.5 | 3.1 |
|  | 10 Hz | 8.1 | 1.9 |
|  | Inactivated state | 2.4 | 1.2 |
| 534 | Tonic | >10 | 8.1 |
|  | 10 Hz | 7.1 | 4.1 |
|  | Inactivated state | 2.1 | 2.3 |
| 536 | Tonic | >30 | 21.4 |
|  | 10 Hz | 1.7 | 3.7 |
|  | Inactivated state | 0.4 | 1.3 |
| 523 | Tonic | >10 | >10 |
|  | 10 Hz | ≈10.0 | 7.6 |
|  | Inactivated state | 4.2 | 2.0 |
| 530 | Tonic | 7.8 | 2.9 |
|  | 10 Hz | 2.9 | 1.7 |
|  | Inactivated state | 1.1 | 0.8 |
| 551 | Tonic | ≈10.1 | 5.6 |
|  | 10 Hz | 4.9 | 2.0 |
|  | Inactivated state | 2.1 | 1.1 |
| 538 | Tonic | >10 | >10 |
|  | 10 Hz | >10 | >10 |

TABLE 3.1-continued

Inhibition of Na$_v$1.2 and Na$_v$1.6 channels

| Compound | Type of Block | IC$_{50}$ (μM) Na$_v$1.2 | Na$_v$1.6 |
|---|---|---|---|
|  | Inactivated state | ≈10.2 | >10 |
| 540 | Tonic | 23.5 | 287.1 |
|  | 10 Hz | 2.3 | 141.5 |
|  | Inactivated state | 1.2 | 80.5 |
| 555 | Tonic | >10 | >10 |
|  | 10 Hz | >10 | >10 |
|  | Inactivated state | 9.3 | 3.7 |
| 553 | Tonic | 3.6 | 1.6 |
|  | 10 Hz | 1.2 | 1.0 |
|  | Inactivated state | 0.2 | 0.3 |
| 554 | Tonic | >1000 | >1000 |
|  | 10 Hz | 32.2 | >1000 |
|  | Inactivated state | 1.4 | >1000 |
| 562 | Tonic | >30 | >30 |
|  | 10 Hz | 1.2 | 1.3 |
|  | Inactivated state | 0.1 | 0.1 |
| 556 | Tonic | >30 | >30 |
|  | 10 Hz | 4.5 | >30 |
|  | Inactivated state | 2.1 | 8.0 |
| 557 | Tonic | >30 | >30 |
|  | 10 Hz | 9.3 | >30 |
|  | Inactivated state | 3.2 | >30 |
| 558 | Tonic | 1.2 | 0.4 |
|  | 10 Hz | 0.6 | 0.4 |
|  | Inactivated state | 0.2 | 0.3 |
| 642 | Tonic | >10 | >10 |
|  | 10 Hz | >10 | >10 |
|  | Inactivated state | >10 | >10 |
| 643 | Tonic | >10 | >10 |
|  | 10 Hz | >10 | >10 |
|  | Inactivated state | >10 | >10 |
| 644 | Tonic | >10 | >10 |
|  | 10 Hz | >10 | >10 |
|  | Inactivated state | >10 | >10 |
| 645 | Tonic | >10 | >10 |
|  | 10 Hz | >10 | >10 |
|  | Inactivated state | >10 | >10 |

The invention claimed is:

1. A compound selected from the group consisting of

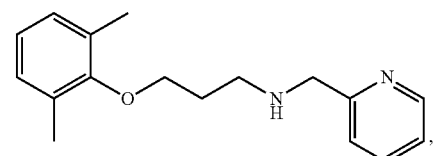,

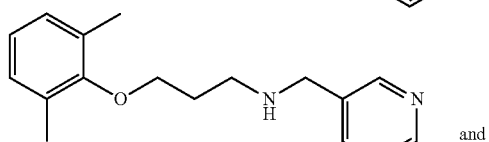 and

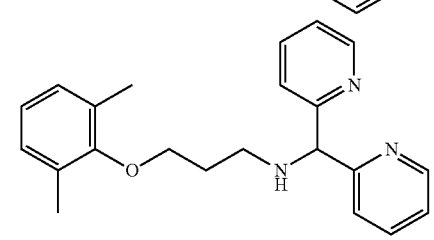

or a pharmaceutically acceptable salt or solvate thereof.

2. A compound having the formula

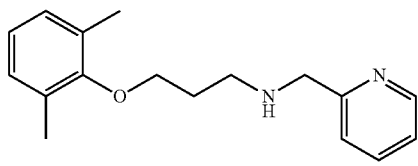 [SMILES: Cc1cccc(C)c1OCCCNCc1ccccn1]

or a pharmaceutically acceptable salt or solvate thereof.

3. A composition comprising the compound according to claim 1, or a pharmaceutically acceptable salt or solvate thereof together with a pharmaceutically acceptable additive.

4. A method for preventing sodium ion influx into a cell by blocking or modulating the activity of one or more sodium channel sub-types, said method comprising contacting said cell with the compound according to claim 1, or a pharmaceutically acceptable salt or solvate thereof.

5. A method for treating a disease or disorder which is mediated by sodium channel activity, in a subject in need thereof, comprising administering to said subject the compound according to claim 1, or a pharmaceutically acceptable salt or solvate thereof, wherein the disease or disorder is an epileptic seizure.

* * * * *